(12) United States Patent
Hayakawa et al.

(10) Patent No.: US 11,780,719 B2
(45) Date of Patent: Oct. 10, 2023

(54) ASEPTIC FILLING APPARATUS AND METHOD OF DECONTAMINATING THE SAME

(71) Applicant: Dai Nippon Printing Co., Ltd., Tokyo (JP)

(72) Inventors: Atsushi Hayakawa, Tokyo (JP); Ryuichi Tamagawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 286 days.

(21) Appl. No.: 17/210,694

(22) Filed: Mar. 24, 2021

(65) Prior Publication Data
US 2021/0229969 A1 Jul. 29, 2021

Related U.S. Application Data

(62) Division of application No. 15/745,819, filed as application No. PCT/JP2016/077249 on Sep. 15, 2016, now Pat. No. 11,014,797.

(30) Foreign Application Priority Data

Sep. 17, 2015 (JP) ................................. 2015-184339
Nov. 18, 2015 (JP) ................................. 2015-226088
Nov. 18, 2015 (JP) ................................. 2015-226089

(51) Int. Cl.
*B67C 3/00* (2006.01)
*A61L 2/04* (2006.01)
(Continued)

(52) U.S. Cl.
CPC ................ *B67C 3/001* (2013.01); *A61L 2/04* (2013.01); *A61L 2/18* (2013.01); *A61L 2/208* (2013.01);
(Continued)

(58) Field of Classification Search
None
See application file for complete search history.

(56) References Cited

U.S. PATENT DOCUMENTS

| 2003/0165400 A1 | 9/2003 | Hayakawa et al. |
| 2007/0193222 A1 | 8/2007 | Till et al. |

(Continued)

FOREIGN PATENT DOCUMENTS

| CN | 104415383 A | 3/2015 |
| JP | H04-253688 A1 | 9/1992 |

(Continued)

OTHER PUBLICATIONS

International Search Report and Written Opinion (Application No. PCT/JP2016/077249) dated Dec. 6, 2016.

*Primary Examiner* — Natasha N Campbell
*Assistant Examiner* — Pradhuman Parihar
(74) *Attorney, Agent, or Firm* — BURR PATENT LAW, PLLC

(57) ABSTRACT

In an aseptic filling apparatus, a CIP of the content filling station is performed after rotation of a wheel in the content filling station is stopped, a COP or SOP of the content filling station is performed while the wheel in the content filling station is rotating immediately after the CIP is completed, an SIP of the content filling station is performed with rotation of the wheel in the content filling station being stopped immediately after the COP or SOP is completed, and one or both of the COP and SOP of the other stations is performed in a predetermined order while wheels in the other stations are rotating in a period from the start of the CIP to the end of the SIP.

9 Claims, 17 Drawing Sheets

(51) Int. Cl.
*A61L 2/18* (2006.01)
*A61L 2/20* (2006.01)
*B08B 3/02* (2006.01)

(52) U.S. Cl.
CPC ............... *B08B 3/02* (2013.01); *B67C 3/005* (2013.01); *A61L 2202/17* (2013.01)

(56) References Cited

U.S. PATENT DOCUMENTS

| | | |
|---|---|---|
| 2011/0094616 A1 | 4/2011 | Hayakawa et al. |
| 2011/0289883 A1 | 12/2011 | Neubauer |
| 2015/0069271 A1 | 3/2015 | Soellner et al. |
| 2015/0298178 A1 | 10/2015 | Hayakawa |
| 2016/0046475 A1* | 2/2016 | Hayakawa ............... B67C 3/005 134/22.18 |
| 2016/0185584 A1 | 6/2016 | Hayakawa et al. |
| 2016/0257055 A1* | 9/2016 | Hayakawa ............... A61L 2/208 |

FOREIGN PATENT DOCUMENTS

| | | | |
|---|---|---|---|
| JP | 2000-153245 A1 | 6/2000 | |
| JP | 2001-039414 A1 | 2/2001 | |
| JP | 3315918 B2 | 8/2002 | |
| JP | 2004-299723 A1 | 10/2004 | |
| JP | 2006-111295 A1 | 4/2006 | |
| JP | 3876329 B2 | 1/2007 | |
| JP | 2007-022600 A1 | 2/2007 | |
| JP | 2007-331801 A1 | 12/2007 | |
| JP | 2010-189034 A1 | 9/2010 | |
| JP | 5328105 B2 | 10/2013 | |
| JP | 2014-055026 A1 | 3/2014 | |
| JP | 5582213 B1 | 9/2014 | |
| JP | 2014-189328 A1 | 10/2014 | |
| JP | 2015-116816 A1 | 6/2015 | |
| JP | 2015-157651 A1 | 9/2015 | |
| JP | 2015-174692 A1 | 10/2015 | |
| WO | 2014/077319 A1 | 5/2014 | |
| WO | 2014/098058 A1 | 6/2014 | |
| WO | WO-2015072506 A1 * | 5/2015 | ............... A61L 2/04 |

* cited by examiner

FIG.6

| SWITCH TIME BETWEEN PRODUCTIONS | CONTENT FILLING ST. | CONTAINER SEALING ST. | CONTAINER STERILIZING ST. | LID STERILIZING ST. |
|---|---|---|---|---|
| | END OF MANUFACTURE | | | |
| 0 h | CIP | RAISING OF TEMPERATURE } SOP | | |
| | | SPRAYING OF HYDROGEN PEROXIDE SOLUTION | | |
| 1 h | | DRYING | | |
| 2 h | CLEANING WITH PERACETIC ACID } SOP | CLEANING WITH PERACETIC ACID } SOP | | |
| 3 h | | | CLEANING WITH PERACETIC ACID } SOP | CLEANING WITH PERACETIC ACID } SOP |
| 4 h | CLEANING WITH ASEPTIC WATER | CLEANING WITH ASEPTIC WATER | | |
| 5 h | | | CLEANING WITH ASEPTIC WATER | CLEANING WITH ASEPTIC WATER |
| 6 h | SIP | RAISING OF TEMPERATURE } SOP | | |
| | | SPRAYING OF HYDROGEN PEROXIDE SOLUTION | | |
| | | DRYING | | |
| | START OF MANUFACTURE | | | |

PRIOR ART

FIG.11

| SWITCH TIME BETWEEN PRODUCTIONS | CONTENT FILLING ST. | CONTAINER SEALING ST. | CONTAINER STERILIZING ST. | LID STERILIZING ST. | CONTAINER MOLDING ST |
|---|---|---|---|---|---|
| | END OF MANUFACTURE | | | | |
| 0 h | CIP | | | | |
| 1 h | | | | | |
| 2 h | CLEANING WITH PERACETIC ACID } SOP | CLEANING WITH PERACETIC ACID } SOP | CLEANING WITH PERACETIC ACID } SOP | | |
| 3 h | | | | CLEANING WITH PERACETIC ACID } SOP | |
| 4 h | CLEANING WITH ASEPTIC WATER | CLEANING WITH ASEPTIC WATER | CLEANING WITH ASEPTIC WATER | | } SOP |
| 5 h | | | | CLEANING WITH ASEPTIC WATER | |
| 6 h | SIP | | | | |
| | START OF MANUFACTURE | | | | |

ASEPTIC FILLING APPARATUS AND METHOD OF DECONTAMINATING THE SAME

CROSS REFERENCE TO RELATED APPLICATION

This application is a division of U.S. application Ser. No. 15/745,819, filed Jan. 18, 2018, which in turn is the National Stage entry of International Application No. PCT/JP2016/077249, filed Sep. 15, 2016, which designated the United States, the entireties of which are incorporated herein by reference.

FIELD OF THE INVENTION

The present invention relates to an aseptic filling apparatus and a method of decontaminating the aseptic filling apparatus by cleaning and sterilization.

BACKGROUND OF THE INVENTION

An aseptic filling apparatus includes a wheel train that conveys a container such as a bottle in one direction, and a container sterilizing station, a content filling station and a container sealing station are arranged from the upstream side to the downstream side of the flow of the container fed by rotation of the wheels in the wheel train.

In the container sterilizing station, there is arranged a nozzle that blasts mist of a hydrogen peroxide solution, which is a sterilizer, to the container moving around a wheel. The content filling station is configured as a filler in which a content filling nozzle rotates around a wheel. The container sealing station is configured as a capper that screws a cap onto a mouth portion of the bottle.

In addition, there are provided chambers that cover the wheel train and portions from the container sterilizing station to the container sealing station (see Patent Literatures 1 and 2, for example).

In the content filling station in the aseptic filling apparatus, there are provided a large number of filling nozzles that are arranged at regular intervals along the circumference of a predetermined wheel to fill a large number of bottles with a drink, which is a content, at high rate.

All the filling nozzles rotate at high speed along with the wheel to fill the bottles traveling in synchronization with the filling nozzles with a fixed amount of drink.

The drink is supplied from a preparation apparatus therefor to the filling nozzles in the content filling station through drink supply piping. The drink supply piping is subjected to a CIP (Cleaning in Place) to remove any remainder or foreign matters and is further subjected to an SIP (Sterilizing in Place) to be sterilized at regular intervals or when to change the kind of the drink (see Patent Literatures 3, 4 and 5, for example).

The CIP is performed by flowing a cleaning liquid through a flow path from the interior of the drink supply piping to the filling nozzles in the filler, the cleaning liquid containing water and an alkali agent such as sodium hydroxide or potassium hydroxide or an acidic agent such as nitric acid as an additive. In this way, any remainder of the previously used drink or the like adhering to the interior of the drink supply piping is removed (see Patent Literatures 3, 4 and 5, for example).

The SIP is performed by flowing a vapor, hot water or the like through the piping cleaned by the CIP, and the interior of the drink supply piping is sterilized by being heated by the vapor, hot water or the like (see the paragraph [0003] in Patent Literature 5).

Specifically, the CIP and SIP of the interior of the drink supply piping is performed as described below.

Since a liquid needs to be circulated in the drink supply piping and a waste liquid needs to be collected, a cup is placed over the nozzle mouth of each filling nozzle at rest. The cups are arranged so as to be rotatable with the filling nozzles. A manifold that rotates with the filling nozzles and the cups is provided in advance around a pivot around which the filling nozzles rotate. The cup is coupled to the manifold by a pipe, and the manifold is connected to a cleaning-liquid reservoir tank and a pump by a pipe that can be opened and closed. The cleaning-liquid reservoir tank and the pump are fixed to a machine casing or chamber of the content filling station.

When performing the CIP or SIP, rotation of the filling nozzles and the manifold is stopped, the cups are automatically placed on the nozzle mouths to establish a communication between the cups and the manifold, and the manifold and the cleaning-liquid reservoir tank are connected to each other by the pipe.

Then, the cleaning liquid flows from the cleaning-liquid reservoir tank into the drink supply piping, further flows into the filling nozzles and then into the manifold through the nozzle mouths and the cups and thus circulates for a predetermined time. In this way, the CIP of the interior of the drink supply piping and the filling nozzles is performed.

When performing the SIP, hot water or the like is flowed into the drink supply piping and the filling nozzles as in the case of the CIP described above. In this way, the interior of the drink supply piping and the filling nozzles is sterilized.

On the other hand, in the chamber, a COP (Cleaning out of Place) and an SOP (Sterilizing out of Place) are performed to decontaminate the outer surface of the content filling station or the like and the inner wall of the chamber (see Patent Literatures 6, 7, 8 and 9, for example).

To perform the COP and the SOP, various kinds of injection nozzles are arranged in the chamber at different locations. When performing the COP and the SOP, a chemical agent, such as an alkali cleaner, a peracetic acid cleaner or a hydrogen peroxide solution, aseptic water and the like are successively sprayed or injected like a shower in the chamber. The mist, shower or the like of the chemical agent or water cleans and sterilizes the inner wall of the chamber and the surface of equipment such as the filler.

As described above, after the CIP, SIP, COP and SOP of the aseptic filling apparatus are performed, the aseptic filling apparatus starts filling a bottle with a drink, the sterilized bottle is filled in an aseptic environment, and an aseptic bottled drink is produced.

CITATION LIST

Patent Literature

Patent Literature 1: Japanese Patent Laid-Open No. 2001-39414
Patent Literature 2: Japanese Patent Laid-Open No. 2006-111295
Patent Literature 3: Japanese Patent Laid-Open No. 2007-331801
Patent Literature 4: Japanese Patent Laid-Open No. 2000-153245
Patent Literature 5: Japanese Patent Laid-Open No. 2007-22600

Patent Literature 6: Japanese Patent No. 3315918
Patent Literature 7: Japanese Patent Laid-Open No. 2004-299723
Patent Literature 8: Japanese Patent Laid-Open No. 2010-189034
Patent Literature 9: Japanese Patent No. 5582213

SUMMARY OF THE INVENTION

Technical Problem

As described above, when the CIP and SIP of the interior of the drink supply piping are performed, the manifold and the cleaning-liquid supply source are connected by a pipe, and thus, rotation of the wheel in the content filling station is stopped to stop rotation of the filling nozzles or the like. In addition, since the wheels of the conventional wheel train are always engaged for power transmission between the container sterilizing station, the content filling station and the container sealing station, if the wheel in the content filling station is stopped, the wheels in the container sterilizing station and the container sealing station are also stopped.

Thus, as shown in FIG. 11, when the CIP or SIP of the drink supply piping is performed, the COP and the SOP are set in the standby state, and the COP and the SOP are started after the CIP or SIP is completed.

This is because, if the COP or SOP of the interior of the chamber is performed at the same time as the CIP or SIP, since the wheels are stopped, the cleaning liquid or sterilizing liquid does not spread into every corner of the container sterilizing station, the content filling station and the container sealing station, and the stations tends to be poorly cleaned and sterilized.

In particular, the filling nozzles in the content filling station have a complicated shape and structure, so that even if the COP or SOP is performed on the content filling station at rest, the filling nozzles tends to be poorly cleaned and sterilized. Since the filling nozzles are used to fill the bottles with a drink, if bacteria or foreign matters remain on the surface of the filling nozzles, the bacteria or foreign matters are likely to enter the bottles.

To avoid this, conventionally, the COP or SOP of the interior of the chamber is performed in a state where the filling nozzles or the like are allowed to rotate after the CIP and SIP of the drink supply piping is completed, the pipe connecting the manifold and the cleaning-liquid reservoir tank is disconnected, and then all the wheels of the wheel train are allowed to rotate.

That is, the cleaning liquid or the like is injected from various kinds of nozzles in the chamber for the content filling station in a state where the content filling station is being driven and the filling nozzles are rotating, so that a spray or shower of the cleaning liquid or the like spreads into every corner of the content filling station, in particular, every corner of the filling nozzles, and the content filling station is appropriately cleaned and sterilized. Similarly, if the cleaning liquid or the like is injected from various kinds of nozzles in the chamber for the container sterilizing station while the wheel in the container sterilizing station is rotating, a spray or shower of the cleaning liquid or the like spreads into every corner of the container sterilizing station, and the container sterilizing station is appropriately cleaned and sterilized. Furthermore, if the cleaning liquid or the like is injected from various kinds of nozzles in the chamber for the container sealing station while the wheel in the container sealing station is rotating, a spray or shower of the cleaning liquid or the like spreads into every corner of the container sterilizing station, and the container sterilizing station is appropriately cleaned and sterilized.

However, if the COP and the SOP of the interior of the chamber are performed after the CIP or SIP of the drink supply piping is completed, the downtime (time out of production) of the aseptic filling apparatus is elongated, and the productivity of the bottled drink is reduced.

Now, FIG. 6 shows an example of a decontamination operation such as CIP conventionally performed on the aseptic filling apparatus.

As shown in FIG. 6, to start manufacture of another kind of bottled drink after manufacture of a kind of bottled drink is completed, the operation of the content filling station is stopped to perform the CIP of the drink supply piping when the manufacture of the previous bottled drink is completed.

After the CIP is completed, operation of the content filling station is started, and the SOP (or COP) is performed by successively blasting peracetic acid and aseptic water to the filling nozzles or the like that are rotating.

When the SOP (or COP) of the content filling station is completed, the operation of the content filling station is stopped to perform the SIP of the drink supply piping.

On the other hand, during the CIP or SIP of the content filling station described above, the wheels in the stations other than the content filling station, such as the container sealing station, are stopped so that those stations are at rest, and a spray of a hydrogen peroxide solution or gas or mist or the like of hydrogen peroxide, or the like is blasted to those stations at rest to perform the SOP (or COP) thereof.

Furthermore, a method in which the SOP is performed between the CIP and the SIP is also known. The SOP is performed between the CIP and the SIP, because if the cleaning liquid used in the CIP or any waste liquid leaks at the connection between a cup and a nozzle mouth, for example, the waste liquid or the like can adhere to equipment or the like in the content filling station and enter the drink or container during the subsequent filling operation. The SOP between the SIP and the CIP can wash the waste liquid or the like from the equipment or the like in the content filling station, so that the sterilization by the SIP can be performed in a state where the exterior of the equipment or the like in the content filling station is kept clean.

Until the SIP is performed after the CIP of the interior of the drink supply piping is completed, as shown in FIG. 12, the interior of the piping is rinsed by water supplied into the drink supply piping from a final stage of the CIP, thereby removing the waste liquid, the cleaning liquid and the like from the interior of the drink supply piping and cooling the interior of the piping. Supply of water into the piping is then started, and the temperature of the water is gradually raised to a temperature required for sterilization in the subsequent SIP.

The same SOP (or COP) as the SOP (or COP) of the content filling station described above is performed on the other stations. In this process, the other stations are being driven as with the content filling station. The SOP (or COP) is performed stepwise on the other stations being driven in a period from the end of the CIP to the start of the SIP of the content filling station.

The SOP (or COP) is performed stepwise because it is difficult to prepare a large amount of peracetic acid or other sterilizer and aseptic water supplied to all the stations at the same time. Thus, after peracetic acid is supplied stepwise to the stations, aseptic water is supplied stepwise to the stations.

Due to the circumstances described above, the decontamination operation performed on the aseptic filling apparatus takes about 6 hours in the example shown in FIG. That is, the downtime of the aseptic filling apparatus is significantly elongated, the decontamination operation is a cause of reduction of the productivity of the bottled drink.

Thus, an object of the present invention is to provide an aseptic filling apparatus and a method of decontaminating the same that can solve the problems described above.

Solution to Problem

To achieve the object described above, the present invention adopts the configurations described below.

Note that reference numerals in parentheses are given to facilitate understanding of the present invention and are not intended to limit the scope of the present invention.

Specifically, the invention according to a first aspect of the present invention adopts a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein a CIP (Step S1) of the content filling station (6) is performed after rotation of a wheel (9) in the content filling station (6) is stopped, a COP or SOP (Step S2) of the content filling station (6) is performed while the wheel (9) in the content filling station (6) is rotating immediately after the CIP (Step S1) is completed, an SIP (Step S3) of the content filling station (6) is performed with rotation of the wheel (9) in the content filling station (6) being stopped immediately after the COP or SOP (Step S2) is completed, and one or both of the COP and SOP (Steps S4, S5, S6, S7) of the other stations (5, 7) is performed in a predetermined order while wheels (12, 13, 17 and the like) in the other stations (5, 7, 53) is rotating in a period from the start of the CIP (Step S1) to the end of the SIP (Step S3).

According to a second aspect of the present invention, in the method of decontaminating an aseptic filling apparatus according to the first aspect of the present invention, the SOP (Step S2) of the content filling station (6) and the SOP (Step S2) of the other stations (5, 7, 53) may be performed stepwise in a period from the start of the SOP (Step S2) to the end of the SIP (Step S3) of the content filling station (6).

According to a third aspect of the present invention, in the method of decontaminating an aseptic filling apparatus according to the first aspect of the present invention, the SOP (Step S2) of the content filling station (6) and the SOP (Steps S5, S6, S7) of the other stations (5, 7, 53) may be performed in parallel between the stations (5, 6, 7, 53).

According to a fourth aspect of the present invention, in the method of decontaminating an aseptic filling apparatus according to the second or third aspects of the present invention, wherein the SOP may be performed by blasting of a sterilizer and blasting of aseptic water.

The invention according to a fifth aspect of the present invention adopts a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein a CIP (Step S1) of the content filling station (6) is performed after rotation of a wheel (9) in the content filling station (6) is stopped, the temperature of a cleaning liquid is raised to a temperature required for an SIP subsequent to the CIP from an early stage or a middle of the CIP, the SIP (Step S2) of the content filling station (6) is performed to sterilize the content filling station (6) and the cleaning liquid is removed with rotation of the wheel (9) in the content filling station (6) kept stopped, and one or both of a COP and an SOP (Step S3) of the content filling station (6) is performed in a predetermined order while the wheel (9) in the content filling station (6) is rotating immediately after the SIP (Step S2) is completed.

The invention according to a sixth aspect of the present invention adopts a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein an SIP (Step S1), which serves also as a CIP, of the content filling station (6) is performed after rotation of a wheel (9) in the content filling station (6) is stopped, and one or both of a COP and an SOP (Step S2) of the content filling station (6) is performed in a predetermined order while the content filling station (6) is rotating immediately after the SIP (Step S1) is completed.

According to a seventh aspect of the present invention, in the method of decontaminating an aseptic filling apparatus according to the fifth or sixth aspects of the present invention, the SOP (Step S3) of the content filling station (6) and the SOP (Steps S5, S6, S7) of the other stations (5, 7, 53) may be performed stepwise immediately after the SIP (Step S2) of the content filling station (6) is completed.

According to an eighth aspect of the present invention, in the method of decontaminating an aseptic filling apparatus according to the fifth or sixth aspects of the present invention, wherein the SOP (Step S3) of the content filling station (6) and the SOP (Steps S5, S6, S7) of the other stations (5, 7, 53) may be performed in parallel with each other immediately after the SIP (Step S2) of the content filling station (6) is completed.

According to a ninth aspect of the present invention, in the method of decontaminating an aseptic filling apparatus according to the seventh or eighth aspects of the present invention, the SOP may be performed by blasting of hot water or a sterilizer and blasting of aseptic water.

According to a tenth aspect of the present invention, in the method of decontaminating an aseptic filling apparatus according to the first, fifth and sixth aspects of the present invention, the SOP (Step S4) of the other stations (5, 7, 53) may be performed while the CIP (Step S1) or SIP (Step S3) of the content filling station (6) is being performed, and the SOP (Step S4) may be performed by blasting of gas or mist of a sterilizer containing hydrogen peroxide.

According to an eleventh aspect of the present invention, in the method of decontaminating an aseptic filling apparatus according to the first, fifth and sixth aspects of the present invention, aseptic air may be constantly blasted to the content filling station (6) in the chamber (21).

According to a twelfth aspect of the present invention, in the method of decontaminating an aseptic filling apparatus according to the first, fifth and sixth aspects of the present invention, a clutch that connects and disconnects transmission of power between wheels may be provided between the wheel (9) in the content filling station (6) and another wheel (12, 13, 17 or the like), and the clutch may be disconnected to stop rotation of the wheel (9) in the content filling station (6).

According to a thirteenth aspect of the present invention, in the method of decontaminating an aseptic filling apparatus according to the first, fifth and sixth aspects of the present invention, the wheels (12, 13, 9, 17 and the like) in the wheel train may be capable of being rotated independently of each other by a dedicated servo motor, and the dedicated servo motor may be stopped to stop rotation of the wheel (9) in the content filling station (6).

According to a fourteenth aspect of the present invention, in the method of decontaminating an aseptic filling apparatus according to the first, fifth and sixth aspects of the present invention, of the various kinds of stations, the stations other than the content filling station (6) may be a container molding station, a container sterilizing station (5), a container sealing station (7) or a lid sterilizing station (53).

The invention according to a fifteenth aspect of the present invention adopts an aseptic filling apparatus, comprising various kinds of stations including a content filling station (6) arranged from an upstream side to a downstream side of a flow of a preform or container fed by rotation of wheels (12, 13, 9, 17 and the like) in a wheel train, each of the various kinds of stations (5, 6, 7, 53) being covered by a chamber (20, 21, 56), wherein a CIP (Step S1) of the content filling station (6) is performed after rotation of a wheel (9) in the content filling station (6) is stopped, a COP or SOP (Step S2) of the content filling station (6) is performed while the wheel (9) in the content filling station (6) is rotating immediately after the CIP (Step S1) is completed, an SIP (Step S3) of the content filling station (6) is performed with rotation of the wheel (9) in the content filling station (6) being stopped immediately after the COP or SOP (Step S2) is completed, and one or both of the COP and SOP (Step S2) of the other stations (5, 7, 53) is performed in a predetermined order while wheels (12, 13, 17 and the like) in the other stations (5, 7, 53) is rotating in a period from the start of the CIP (Step S2) to the end of the SIP (Step S3).

According to a sixteenth aspect of the present invention, in the aseptic filling apparatus according to the fifteenth aspect of the present invention, the SOP (Step S2) of the content filling station (6) and the SOP (Steps S5, S6, S7) of the other stations (5, 7, 53) may be performed stepwise in a period from the start of the SOP (Step S2) to the end of the SIP (Step S3) of the content filling station (6).

According to a seventeenth aspect of the present invention, in the aseptic filling apparatus according to the fifteenth aspect of the present invention, the SOP (Step S2) of the content filling station (6) and the SOP (Steps S5, S6, S7) of the other stations (5, 7, 53) may be performed in parallel between the stations (5, 6, 7, 53).

According to an eighteenth aspect of the present invention, in the aseptic filling apparatus according to the sixteenth or seventeenth aspects of the present invention, the SOP may be performed by blasting of a sterilizer and blasting of aseptic water.

The invention according to a nineteenth aspect of the present invention adopts an aseptic filling apparatus, comprising various kinds of stations including a content filling station (6) arranged from an upstream side to a downstream side of a flow of a preform or container (3) fed by rotation of wheels (12, 13, 9, 17 and the like) in a wheel train, each of the various kinds of stations (5, 6, 7, 53) being covered by a chamber (20, 21, 56), a CIP (Step S1) of the content filling station (6) is performed after rotation of a wheel (9) in the content filling station (6) is stopped, the temperature of a cleaning liquid is raised to a temperature required for an SIP subsequent to the CIP from an early stage or a middle of the CIP, the SIP (Step S2) of the content filling station (6) is performed to sterilize the content filling station (6) and the cleaning liquid is removed with rotation of the wheel (9) in the content filling station (6) kept stopped, and one or both of a COP and an SOP (Step S3) of the content filling station (6) is performed in a predetermined order while the wheel (9) in the content filling station (6) is rotating immediately after the SIP (Step S2) is completed.

The invention according to a twentieth aspect of the present invention adopts an aseptic filling apparatus, comprising various kinds of stations including a content filling station (6) arranged from an upstream side to a downstream side of a flow of a preform or container (3) fed by rotation of wheels (12, 13, 9, 17 and the like) in a wheel train, each of the various kinds of stations (5, 6, 7, 53) being covered by a chamber (20, 21, 56), an SIP (Step S1), which serves also as a CIP, of the content filling station (6) is performed after rotation of a wheel (9) in the content filling station (6) is stopped, and one or both of a COP and an SOP (Step S2) of the content filling station (6) is performed in a predetermined order while the wheel (9) in the content filling station (6) is rotating immediately after the SIP (Step S1) is completed.

According to a twenty-first aspect of the present invention, in the aseptic filling apparatus according to the nineteenth or twentieth aspects of the present invention, the SOP (Step S3) of the content filling station (6) and the SOP (Steps S5, S6, S7) of the other stations (5, 7, 53) may be performed stepwise immediately after the SIP (Step S2) of the content filling station (6) is completed.

According to a twenty-second aspect of the present invention, in the aseptic filling apparatus according to the nineteenth or twentieth aspects of the present invention, the SOP (Step S3) of the content filling station (6) and the SOP (Steps S5, S6, S7) of the other stations (5, 7, 53) may be performed in parallel with each other immediately after the SIP (Step S2) of the content filling station (6) is completed.

According to a twenty-third aspect of the present invention, in the aseptic filling apparatus according to the nineteenth or twentieth aspects of the present invention, the SOP may be performed by blasting of hot water or a sterilizer and blasting of aseptic water.

According to a twenty-fourth aspect of the present invention, in the aseptic filling apparatus according to the fifteenth, nineteenth and twentieth aspects of the present invention, the SOP (Step S4) of the other stations (5, 7, 53) may be performed while the CIP (Step S1) or SIP (Step S3) of the content filling station (6) is being performed, and the SOP (Step S4) may be performed by blasting of gas or mist of a sterilizer containing hydrogen peroxide.

According to a twenty-fifth aspect of the present invention, in the aseptic filling apparatus according to the fifteenth, nineteenth and twentieth aspects of the present invention, aseptic air may be constantly blasted to the content filling station (6) in the chamber (21).

According to a twenty-sixth aspect of the present invention, in the aseptic filling apparatus according to the fifteenth, nineteenth and twentieth aspects of the present invention, a clutch that connects and disconnects transmission of power between wheels may be provided between the wheel (9) in the content filling station (6) and wheels (12, 13, 17 and the like) in the container sterilizing station (5) and the container sealing station (7), and the clutch may be disconnected to stop rotation of the wheel (9) in the content filling station (6).

According to the twenty-seventh aspect of the present invention, in the aseptic filling apparatus according to the fifteenth, nineteenth and twentieth aspects of the present invention, the wheels (12, 13, 9, 17 and the like) in the wheel train may be capable of being rotated independently of each other by a dedicated servo motor, and the dedicated servo motor may be stopped to stop rotation of the wheel (9) in the content filling station (6).

According to the twenty-eighth aspect of the present invention, in the aseptic filling apparatus according to the fifteenth, nineteenth and twentieth aspects of the present invention, of the various kinds of stations, the stations other than the content filling station (6) may be a container molding station, a container sterilizing station (5), a container sealing station (7) or a lid sterilizing station (53).

Advantageous Effects of Invention

According to the present invention, there is provided a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein a CIP (Step S1) of the content filling station (6) is performed after rotation of a wheel (9) in the content filling station (6) is stopped, a COP or SOP (Step S2) of the content filling station (6) is performed while the wheel (9) in the content filling station (6) is rotating immediately after the CIP (Step S1) is completed, an SIP (Step S3) of the content filling station (6) is performed with rotation of the wheel (9) in the content filling station (6) being stopped immediately after the COP or SOP (Step S2) is completed, and one or both of the COP and SOP (Steps S4, S5, S6, S7) of the other stations (5, 7) is performed in a predetermined order while wheels (12, 13, 17 and the like) in the other stations (5, 7, 53) is rotating in a period from the start of the CIP (Step S1) to the end of the SIP (Step S3). Thus, when the CIP (Step S1) and the SIP (Step S3) of the content filling station (6) are performed, the COP or SOP (Steps S4, S5, S6, S7) of the other stations (5, 7) can be performed with the wheels (12, 13, 17 and the like) rotating, and when the COP or SOP (Step S2) of the content filling station (6) is performed while the wheel (9) in the content filling station is rotating, the COP or SOP (Steps S5, S6, S7) of the other stations (5, 7, 53) can also be performed with the wheels (12, 13, 17 and the like) rotating.

Therefore, the COP or SOP of the various kinds of stations including the content filling station (6) can be efficiently performed, and the cleaning effect and the sterilization effect of the various kinds of stations (5, 6, 7, 53) can be improved. Furthermore, the total time of the COP or SOP (Steps S2, S5, S6, S7) of the various kinds of stations (5, 6, 7, 53) can be reduced, so that the drink or other content filling operation can be started earlier, and the time out of production of the aseptic filling apparatus and the idle time due to changing of the kind of the drink can be reduced to improve the production efficiency.

In addition, according to the present invention, there is provided a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein a CIP (Step S1) of the content filling station (6) is performed after rotation of a wheel (9) in the content filling station (6) is stopped, the temperature of a cleaning liquid is raised to a temperature required for an SIP subsequent to the CIP from an early stage or a middle of the CIP, the SIP (Step S2) of the content filling station (6) is performed to sterilize the content filling station (6) and the cleaning liquid is removed with rotation of the wheel (9) in the content filling station (6) kept stopped, and one or both of a COP and an SOP (Step S3) of the content filling station (6) is performed in a predetermined order while the wheel (9) in the content filling station (6) is rotating immediately after the SIP (Step S2) is completed. Thus, the time required to shift from the CIP (Step S1) to the SIP (Step S2) of the content filling station (6) can be reduced.

Therefore, the cleaning effect and the sterilization effect of the content filling station (6) can be improved. Furthermore, the time required for the decontamination operation can be reduced, so that the drink or other content filling operation can be started earlier, and the time out of production of the aseptic filling apparatus and the idle time due to changing of the kind of the drink can be reduced to improve the production efficiency.

In addition, according to the present invention, there is provided a method of decontaminating an aseptic filling apparatus, the aseptic filling apparatus comprising various kinds of stations including a content filling station (6) arranged from an upstream side to a downstream side of a flow of a preform or container (3) fed by rotation of wheels (12, 13, 9, 17 and the like) in a wheel train, and each of the various kinds of stations being covered by a chamber (20, 21, 56), wherein an SIP (Step S1), which serves also as a CIP, of the content filling station (6) is performed after rotation of a wheel (9) in the content filling station (6) is stopped, and one or both of a COP and an SOP (Step S2) of the content filling station (6) is performed in a predetermined order while the wheel (9) in the content filling station (6) is rotating immediately after the SIP (Step S1) is completed. Thus, the time required to clean and sterilize and thus decontaminate the interior of the piping of the content filling station (6) can be reduced.

Therefore, the time required for the decontamination operation of the content filling station (6) can be reduced, so that the drink or other content filling operation can be started earlier, and the time out of production of the aseptic filling apparatus and the idle time due to changing of the kind of the drink can be reduced to improve the production efficiency.

BRIEF DESCRIPTION OF THE DRAWINGS

FIG. 6 is a flowchart showing a conventional decontaminating method for an aseptic filling apparatus.

FIG. 11 is a flowchart showing a conventional decontaminating method for an aseptic filling apparatus.

DETAILED DESCRIPTION OF THE INVENTION

In the following, embodiments of the present invention will be described with reference to the drawings.

First Embodiment

Figure 1:
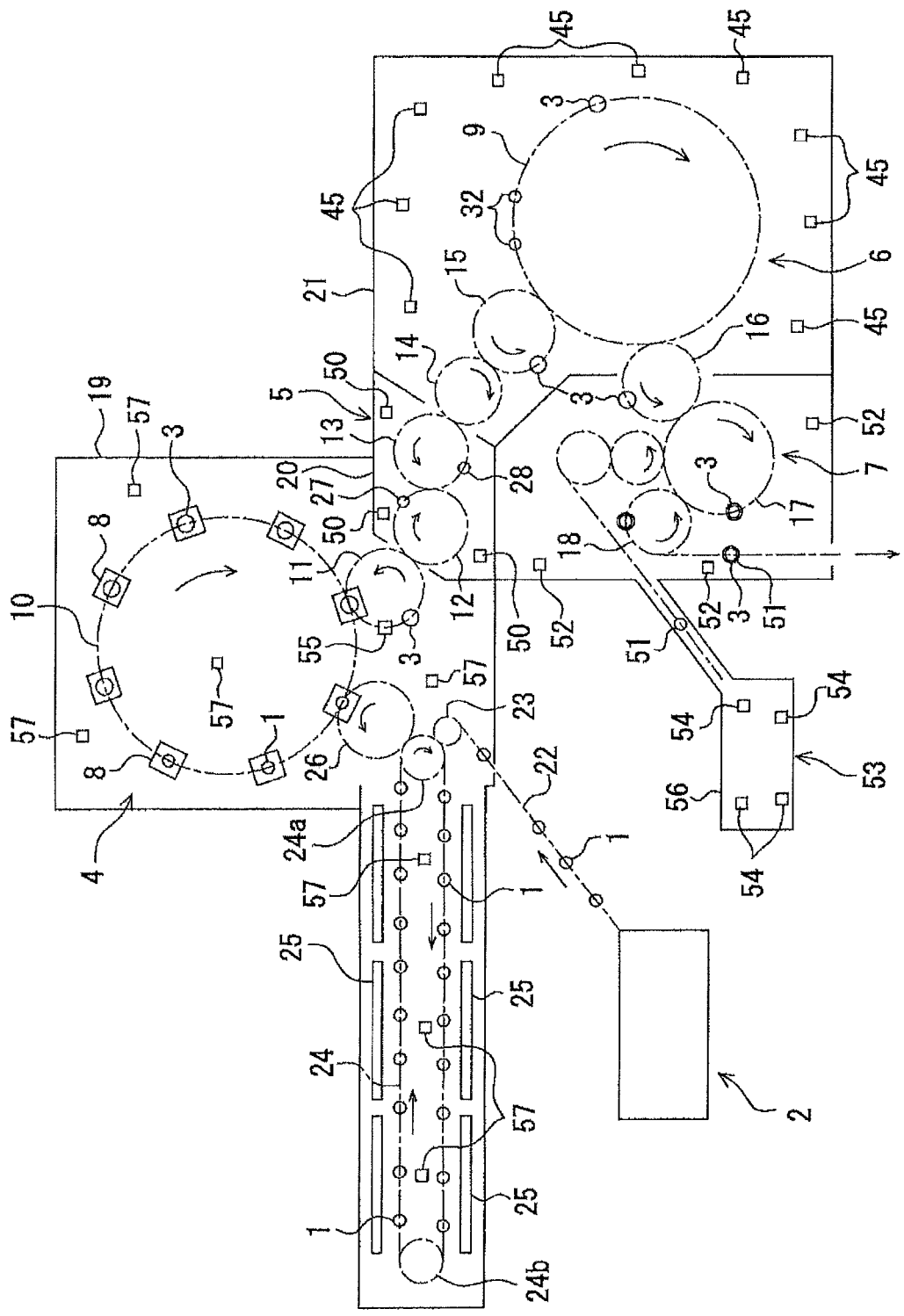
FIG. 1 is a schematic plan view of an aseptic filling apparatus according to the present invention.

As shown in FIG. 1, an aseptic filling apparatus includes a preform supplying station 2 that successively supplies preforms 1 at predetermined intervals, a container molding station 4 that molds the preform 1 into a bottle 3 (see FIG. 3), which is a container, a container sterilizing station 5 that sterilizes the molded bottles 3, a content filling station 6 that fills the sterilized bottles 3 with a content such as a drink, and a container sealing station 7 that seals the bottles 3 filled with the content.

The preform 1 is a bottomed tubular body similar to a test tube and is formed from polyethylene terephthalate (PET), for example, by injection molding or the like. The preform 1 is eventually to be shaped by blow molding into the bottle 3, which is a container, in the container molding station 4. However, a mouth portion 3a (see FIG. 3), a male thread and the like similar to those of the finished bottle 3 are formed on the preform 1 in the early stage of the molding of the preform 1.

Between the preform supplying station 2 and the container sealing station 7, there are provided a preform conveying path that conveys the preform 1 in one direction, a molding die conveying path that conveys in one direction a molding die 8 that molds the preform 1 into the bottle 3, and a bottle conveying path that conveys the bottle 3 molded in the molding die 8 in one direction.

The conveying paths described above are formed by respective conveying means. The preform conveying path is formed by a combination of a shooter and a wheel, for example, and the conveying path from the molding die conveying path to the bottle conveying path is formed by a wheel train formed by a combination of various wheels. Furthermore, a gripper or the like (not shown) for holding the preform 1 or the bottle 3 at the mouth portion 3a thereof during conveyance and passing the preform 1 or the bottle 3 between wheels is provided around a predetermined wheel.

The various conveying paths described above are integrally driven by a motive power from a predetermined power source, and the wheels or the like in the conveying paths are driven in association with each other.

According to the first embodiment, a clutch (not shown) that connects and disconnects transmission of power is provided in a power transmission system for a wheel 9 of the content filling station 6, for example. By disengaging the clutch, rotation of the wheel 9 of the content filling station 6 can be stopped while the other wheels or the like are kept moving.

Instead of providing the clutch, each wheel in the wheel train can be rotated independently of each other by a dedicated servo motor. In that case, rotation of the wheel 9 of the content filling station 6 can be stopped by stopping the relevant dedicated servo motor, while the other dedicated servo motors and the respective other wheels can be kept rotating.

The preform supplying station 2 is disposed along the flow of the preforms 1 traveling on the preform conveying path, the container molding station 4 is disposed along the outer periphery of a predetermined wheel 10 of the molding die conveying path, and the container sterilizing station 5, the content filling station 6 and the container sealing station 7 are disposed along the flow of the bottles 3 fed by rotating wheels 11, 12, 13, 14, 15, 9, 16, 17 and 18 of the wheel train, in this order from upstream to downstream.

Portions of the aseptic filling apparatus from the preform supplying station 2 to the container molding station 4 including the conveying paths for the preforms 1 and the like are covered by a first chamber 19 serving as a protective cover, the container sterilizing station 5 including the bottle conveying path is covered by a second chamber 20, and the content filling station 6 and the container sealing station 7 including the bottle conveying path are covered by a third chamber 21.

The first to third chambers 19, 20 and 21 are arranged adjacent to each other and separated from each other by partition walls. An exhaust duct (not shown) is coupled to the second chamber 20, so that air in the second chamber 20 is constantly discharged to the outside of the second chamber 20 during operation of the aseptic filling apparatus. Furthermore, in the third chamber 21, the content filling station 6 and the container sealing station 7 are separated by a partition wall. During operation of the aseptic filling apparatus, aseptic air is constantly supplied from an aseptic air supply source (not shown) to the part of the third chamber 21 containing the content filling station 6, thereby keeping the interior of the third chamber 21 at a positive pressure. The aseptic air supplied to the part containing the content filling station 6 flows into the part containing the container sealing station 7 through a clearance in the partition wall through which the bottles pass.

The preform conveying path and the preform supplying station 2 of the aseptic filling apparatus will be first described. The preform conveying means includes a shooter 22 that successively supplies preforms 1 at predetermined intervals, a wheel 23 that receives the preforms 1 from a terminal end of the shooter 22 and conveys the preforms 1, and an endless chain 24 that extends in a horizontal direction, receives the preforms 1 from the wheel 23 and transfers the preforms 1.

The endless chain 24 is stretched between a pair of pulleys 24a and 24b that are disposed to be opposed to each other in a horizontal plane, and the shooter 22 is connected to one 24a of the pulleys.

A large number of holding members (not shown) for preforms 1 are attached to the endless chain 24 at regular intervals. Each holding member can rotate on its axis while moving with the endless chain 24. The holding member is formed as a spindle and has a plurality of ball-shaped elastic bodies embedded in an outer surface of a lower portion thereof. Once the holding member is inserted into the mouth portion 3a of the preform 1, the elastic bodies are elastically deformed to hold the preform 1 on the holding member.

The holding member is inserted into the mouth portion 3a of the preform 1 passed from the wheel 23 to the endless chain 24, and thus, the preform 1 is held in an upright position by the holding member.

The endless chain 24 is surrounded by a furnace wall of a heating furnace, and a heater 25 that emits infrared rays is provided all over an inner surface of the furnace wall.

The preform 1 is received by the holding member attached to the endless chain 24 via the shooter 22, travels with endless chain 24 moving and is heated by the heater 25 to a temperature that allows blow molding. Preferably, the preform 1 is uniformly heated by rotating on its axis as the holding member rotates until the temperature of the preform 1 excluding the mouth portion 3a rises to 90° C. to 130° C., which is a temperature range suitable for blow molding. The temperature of the mouth portion 3a is kept to be equal to or lower than 70° C., at which no deformation or the like occurs, so that sealing between the mouth portion 3a and a cap 51 (see FIG. 1) to be fitted on the mouth portion 3a is not compromised.

At a position where the pulley 24a at one end of the endless chain 24 is connected to the return run of the endless chain 24, a wheel 26 that receives the preform 1 heated by the heater 25 and passes the preform 1 to the molding die 8 on the second conveying path is provided adjacent to the pulley 24a.

Next, the molding die conveying path and the container molding station 4 will be described. The molding die conveying path includes a wheel train including a wheel 26 adjacent to the pulley 24a in the preform conveying path and wheels 10 and 11.

A plurality of molding dies 8, which are a plurality of sets of split dies, that receive the preform 1 heated by the heater 25 and blow mold the preform 1 into the bottle 3 are disposed around the wheel 10 at predetermined intervals. The molding dies 8 can rotate at a constant velocity around the wheel 10 as the wheel 10 rotates.

Once the finished bottle 3 is exposed in the molding die 8 opened, the bottle 3 is removed out of the molding die 8 by a gripper disposed around the wheel 11 adjacent to the wheel 10 and passed a gripper around the wheel 12 downstream thereof.

A camera 55 is disposed at a position along the outer periphery of the wheel 11. The camera 55 images a top surface of the mouth portion 3a of the bottle 3, and whether the smoothness of the top surface is appropriate or not is determined based on the image.

Next, the bottle conveying path and the container sterilizing station 5 will be described. The bottle conveying path includes a wheel train including the wheels 11, 12, 13, 14, 15, 9, 16, 17 and 18.

The container sterilizing station 5 includes a sterilizer spraying nozzle 27 and an air rinsing nozzle 28 arranged around the wheels 12 and 13, respectively, in the wheel train.

Figure 2:
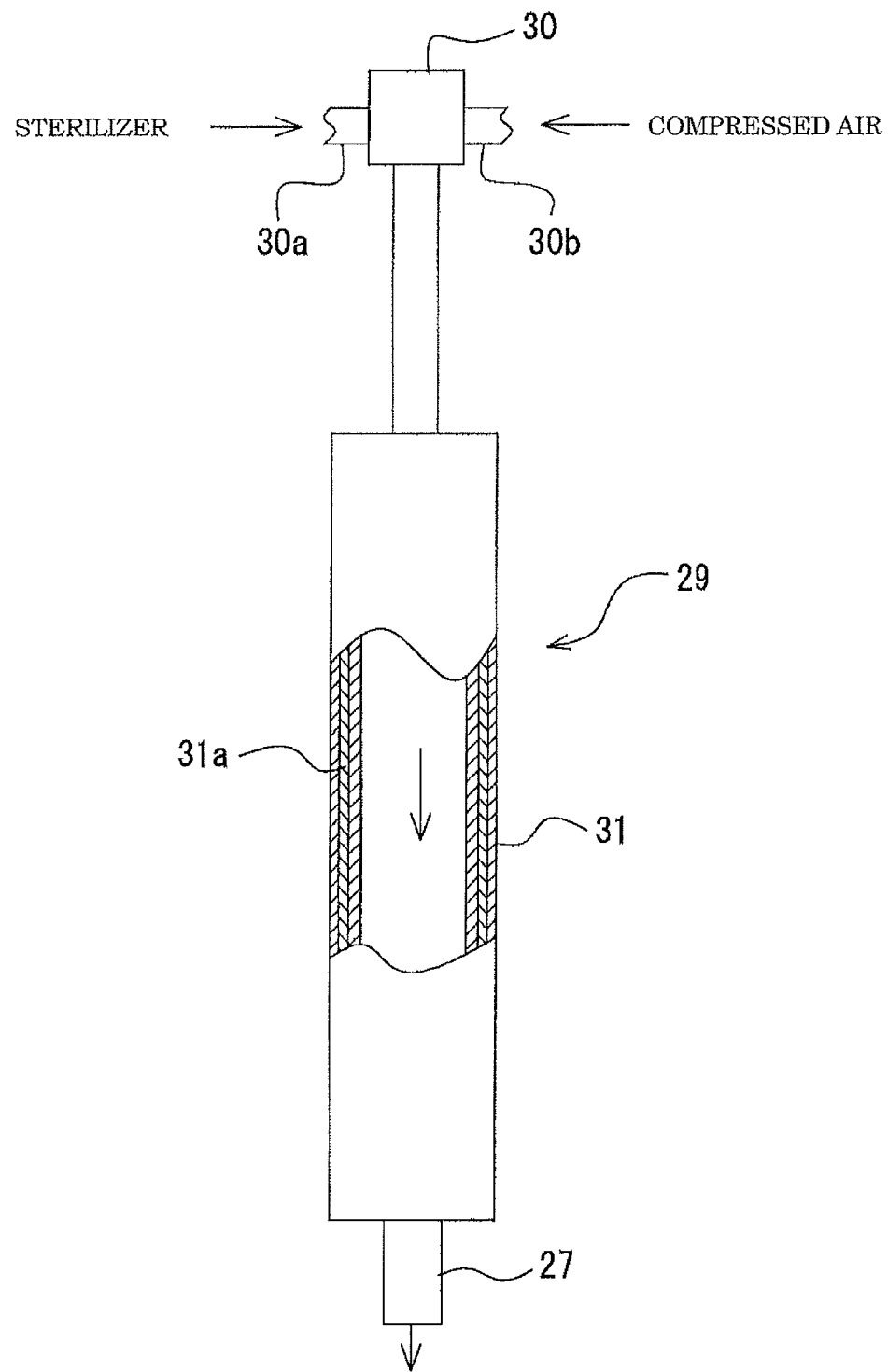
FIG. 2 is a schematic diagram showing a sterilizer vaporizer in the aseptic filling apparatus.

The sterilizer spraying nozzle 27 is disposed with a nozzle injection hole thereof being opposed to the opening of the mouth portion 3a of the bottle 3 traveling around the wheel 12, and a sterilizer vaporizer 29 illustrated in FIG. 2 is connected to the sterilizer spraying nozzle 27 at the upstream side thereof.

The sterilizer effectively contains 1% by mass or more of hydrogen peroxide. Alternatively, the sterilizer may contain one or more of ethanol, peracetic acid, ozone, chlorine dioxide and a chlorine-based sterilizer or a mixture thereof.

The vaporizer 29 includes a hydrogen peroxide supplying portion 30 that is a twin-fluid spray that sprays a hydrogen peroxide solution serving as a sterilizer and a vaporizing portion 31 that vaporizes a spray of hydrogen peroxide supplied from the hydrogen peroxide supplying portion 30 by heating the spray of hydrogen peroxide to a temperature equal to or higher than the boiling point thereof and equal to or lower than the non-degradable temperature thereof. The hydrogen peroxide supplying portion 30 is configured to receive the hydrogen peroxide solution and compressed air from a hydrogen peroxide supply path 30a and a compressed air supply path 30b, respectively, and sprays the hydrogen peroxide solution into the vaporizing portion 31. The vaporizing portion 31 is a pipe that incorporates a heater 31a disposed between inner and outer walls thereof, and heats and vaporizes the spray of hydrogen peroxide blasted into the pipe. The vaporized hydrogen peroxide is ejected in the form of a mist or gas or a mixture thereof from the sterilizer spraying nozzle 27 to the outside of the vaporizer 29. Some of the hydrogen peroxide flows into the bottle 3, and some flows along the outer surface of the bottle 3, so that a uniform coating of hydrogen peroxide is formed on the inner and outer surfaces of the bottle 3.

The air rinsing nozzle 28 is arranged with a nozzle injection hole thereof being opposed to the opening of the mouth portion 3a of the bottle 3 traveling around the wheel 13.

For example, one or more air rinsing nozzles 28 are arranged around the wheel 13. Alternatively, the air rinsing nozzle 28 may be arranged around the wheel 14 or 15 rather than the wheel 13. Air rinsing nozzles 28 may be arranged around the wheels 13, 14 and 15.

While the bottle 3 to which the sterilizer has been blasted is traveling around the wheel 13, aseptic air is blasted to the mouth portion 3a of the bottle 3 from the air rinsing nozzle 28. In this way, the hydrogen peroxide remaining on the inner and outer surfaces of the bottle 3 is decomposed and removed. The sterilized bottle 3 reaches the subsequent content filling station 6 via the wheels 14 and 15.

The aseptic air may be heated air. In that case, the hydrogen peroxide remaining on the inner and outer surfaces of the bottle 3 is activated, so that the effect of sterilization of the bottle 3 is improved.

The container sterilizing station 5 can be omitted if a preform sterilizing station is provided at a position in the travel route of the preforms 1 to sterilize the preforms 1. Although not shown, in the preform sterilizing station, a nozzle for blasting a sterilizer such as hydrogen peroxide to the preforms is provided at a predetermined position around the wheel 23, the endless chain 24 or the wheel 26.

The content filling station 6 is configured as a filler integrated with the wheel 9 in the bottle conveying path.

The content filling station 6 has a large number of filling nozzles 32 around the wheel 9. Each filling nozzle 32 rotates with the wheel 9, and the bottle 3 travels below the filling nozzle 32 in synchronization with the filling nozzle 32. Thus, each filling nozzle 32 fills the relevant bottle 3 with a drink.

Figure 3:
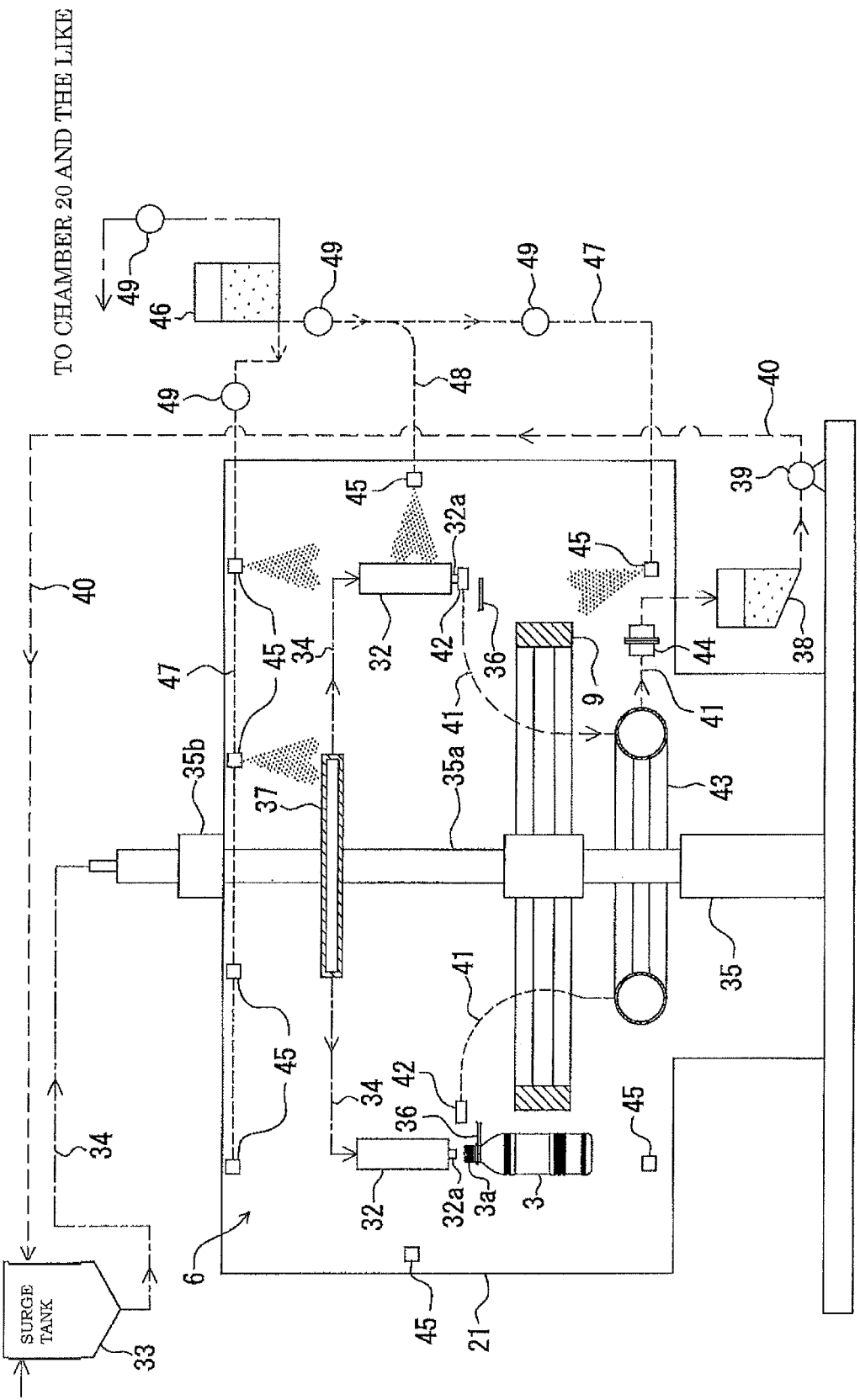
FIG. 3 is a schematic diagram showing a content filling station in the aseptic filling apparatus, the left half showing a state of the station during drink filling and the right half showing a state of the station during cleaning or sterilization.

As shown in FIG. 3, drink supply piping 34 that extends from a drink preparation tank (not shown) is connected to the content filling station 6 via a surge tank 3. The drink prepared in the preparation tank is sterilized in a heater (not shown) in the drink supply piping 34 and then supplied to the content filling station 6.

The filler serving as the content filling station 6 is a unit that fills a large number of bottles 3 with the drink at high rate and includes the wheel 9, which forms a part of the conveying path for the bottles 3, as shown in FIG. 3. The wheel 9 is attached to a part of a pivot 35a of a spindle 35 that stands vertically from a floor surface of the aseptic filling apparatus. Grippers 36 that grasp neck portions of the bottles 3 are arranged at regular intervals around the wheel 9. The grippers 36 can rotate in one direction integrally with the wheel 9. In addition, the large number of filling nozzles 32 are arranged at the same intervals as the grippers 36 around the wheel 9.

An upper part of the spindle 35 is fixed to a casing of the content filling station 6, and a rotary joint 35b is provided between the fixed upper part and an upper end of the pivot 35a. An upper manifold 37 is arranged on the pivot 35a at a position below the rotary joint 35b. A part of the spindle 35 from the top to the upper manifold 37 is hollow, and the drink supply piping 34 is coupled to the top of the spindle 35. The drink supply piping 34 extends from the upper manifold 37 to the filling nozzles 32.

In operation of the content filling station 6, the wheel 9 rotates at high speed, and the bottles 3 grasped by the grippers 36 are conveyed at high speed on the bottle conveying path in synchronization with the rotation of the wheel 9. Since the large number of bottles 3 travels in a line directly below a nozzle mouth 32a of the filling nozzle 32, a predetermined amount of the drink is supplied successively to each bottle 3.

The container sealing station 7 is configured as a capper integrated with the wheel 17 in the bottle conveying path and is covered by the chamber 21, which also covers the content filling station 6.

While the bottle 3 that has been filled with the drink in the content filling station 6 while traveling on the bottle conveying path is traveling around the wheel 17 of the capper, a cap 51 is screwed onto the mouth portion 3a of the bottle 3. In this way, an aseptic bottled drink is finished.

As shown in FIG. 1, the capper is provided with a cap sterilizing station 53, which is a station for sterilizing caps.

The cap 51 that closes the mouth portion 3a of the bottle 3 is previously sterilized in the cap sterilizing station 53 before the cap 51 is supplied to the container sealing station 7. The cap sterilizing station 53 is also covered by a chamber to maintain the aseptic condition of the cap sterilizing station 53.

A large number of caps previously molded are supplied to the cap sterilizing station 53. The caps are sterilized by blasting a spray of a sterilizer such as hydrogen peroxide to the caps traveling in the cap sterilizing station 53 and then blasting aseptic hot air to the caps. The sterilized caps are supplied from the cap sterilizing station 53 to the capper by a shooter or the like.

During manufacture of the bottled drink, aseptic air, desirably aseptic hot air, is constantly blasted from the aseptic air supply source to the content filling station 6 in the chamber 21. This ensures that the atmosphere in the chamber 21 is kept at a positive pressure, and the outside air containing bacteria, dust or the like is prevented from entering the chamber 21. Furthermore, the aseptic air also flows to the container sealing station 7 in the same chamber 21 and the container sterilizing station 5 in the chamber 20, so that the outside air is also prevented from entering the container sealing station 7 and the like. In addition, aseptic air is also constantly supplied into the chamber 56 for the cap sterilizing station 53 from another aseptic air supply source (not shown).

The aseptic filling apparatus is provided with decontaminating apparatuses for the container molding station 4, the container sterilizing station 5, the content filling station 6, the container sealing station 7 and the cap sterilizing station 53 contained in the respective chambers 20, 21 and 56, and the decontaminating apparatus performs a decontamination process including CIP, SIP, COP and SOP at regular intervals or when to change the kind of the drink by stopping the drink filling operation.

The decontaminating apparatus does not need to be provided for all the stations and can be omitted for a station that does not need a decontaminating apparatus.

First, a decontaminating apparatus for the content filling station 6 will be described.

As described above, the drink is supplied from the preparation apparatus to the filling nozzle 32 in the content filling station 6 through the drink supply piping 34. The interior of the drink supply piping 34 is subjected to the CIP, then to the SOP or COP, and eventually to the SIP at regular intervals or when to change the kind of the drink.

In FIG. 3, reference numeral 38 denotes a reservoir tank, which is a supply source of a working fluid serving as a cleaning liquid or sterilizing liquid used for the CIP, and reference numeral 39 denotes a liquid feeding pump. The number of reservoir tanks 38 provided depends on the kind of the working fluid, although only one reservoir tank is shown for convenience of drawing. Illustration of a supply source of the sterilizing fluid such as vapor is omitted.

In FIG. 3, reference numeral 40 denotes a feed pipe that extends from the reservoir tank 38 to the surge tank 33, and reference numeral 41 denotes a return pipe that extends from each filling nozzle 32 to the reservoir tank 38. In cooperation with the drink supply piping 34, the feed pipe 40 and the return pipe 41 form a circulation path for the cleaning liquid or the like.

The return pipe 41 is provided with a cup 42 at a leading end thereof, and the cup 42 can be connected to and separated from the nozzle mouth 32a of the relevant filling nozzle 32. When to perform the CIP or SIP, an actuator (not shown) places each cup 42 over the nozzle mouth 32a at the tip end of the relevant filling nozzle 32 in the content filling station 6, thereby connecting the leading end of the return pipe 41 to the nozzle mouth 32a of the filling nozzle 32. Each cup 42 is coupled to a lower manifold 43 by a flexible pipe that forms a part of the return pipe 41. The lower manifold 43 is attached to the pivot 35a and can rotate integrally with the wheel 9, the filling nozzle 32 and the like.

The return pipe 41 is provided with a disconnectable coupling 44 at a part where the return pipe 41 extends from the lower manifold 43 to the reservoir tank 38. When the CIP or SIP is performed, the coupling 44 is connected. In this state, the wheel 9, the filling nozzles 32 and the like are inhibited from rotating. When the CIP or SIP is completed, and the coupling 44 is disconnected, the wheel 9, the filling nozzles 32 and the like are allowed to rotate.

Figure 4:
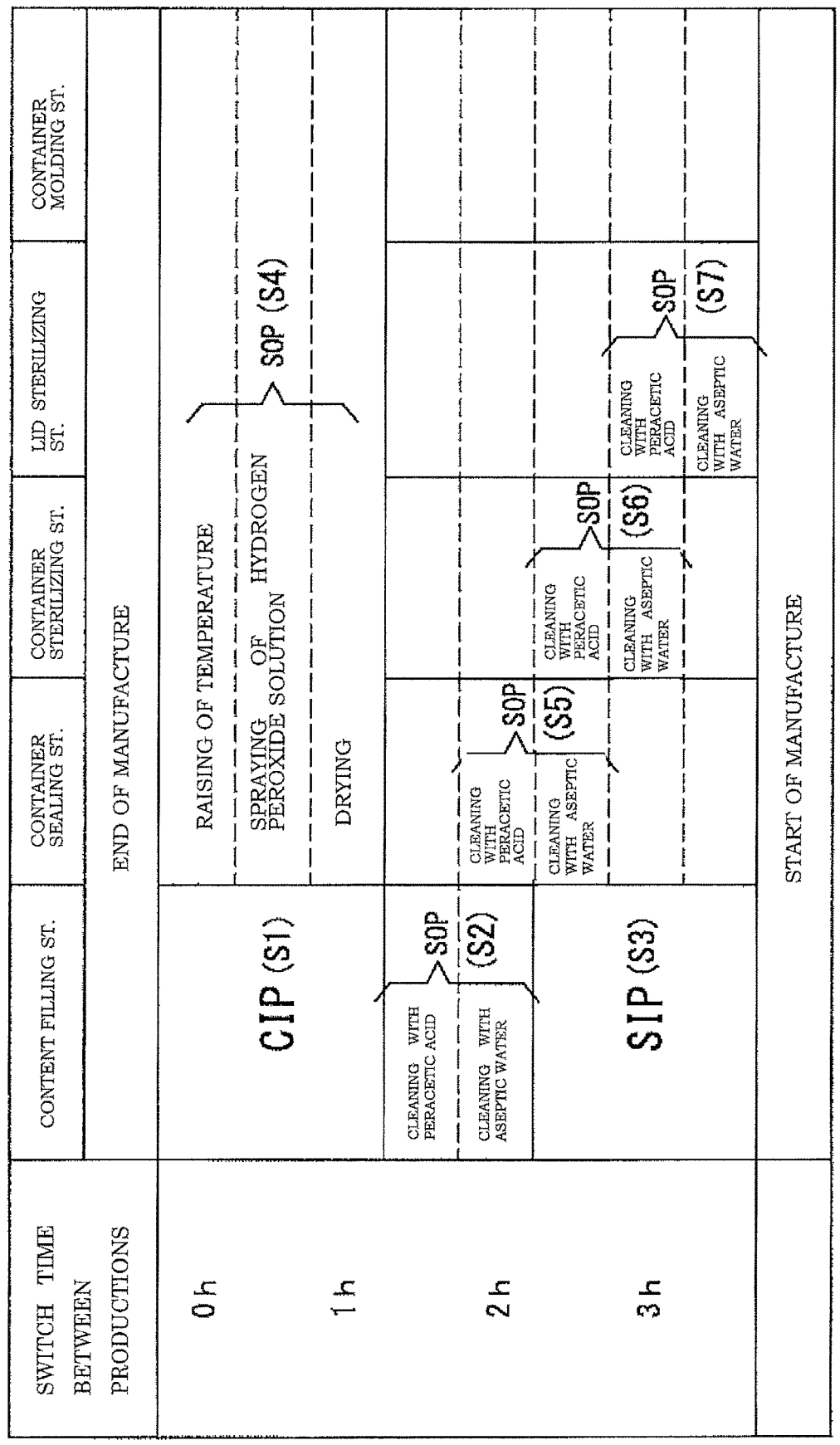
FIG. 4 is a flowchart showing a decontaminating method for the aseptic filling apparatus.

According to the first embodiment, as shown in FIG. 4, a controlling portion (not shown) is programmed to successively perform the CIP, the SOP or COP, and the SIP of the content filling station 6.

First, before starting the CIP (Step S1) of the content filling station 6, the clutch in the power transmission system of the aseptic filling apparatus is disconnected to stop rotation of only the wheel 9 of the content filling station 6, thereby stopping rotation of the filling nozzles 32. In addition, the surge tank 33 is emptied.

As shown in the right half of FIG. 3, the nozzle mouth 32a of the filling nozzle 32 is then closed by the cup 42. In addition, the coupling 44 is connected. In this way, a circulation path for flowing a predetermined working fluid for the CIP such as a cleaning liquid or sterilizing liquid is formed.

The CIP (Step S1) is then started, and a predetermined working fluid such as an alkali cleaner or water is fed from the reservoir tank 38 by a pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean the interior of the drink supply piping 34 including the interior of the filling nozzles 32.

Immediately after the CIP (Step S1) is completed, the SOP or COP (Step S2) (described later) is performed. Immediately after the SOP or COP is completed, the SIP (Step S3) is performed. The SIP is performed by passing the sterilizing working fluid such as hot water or vapor through the drink supply piping 34. The hot water or the like passing through the drink supply piping 34 sterilizes the interior of the drink supply piping 34. Illustration of a supply source of hot water, vapor or the like is omitted.

In FIG. 3, reference numeral 45 denotes an injection nozzle for the SOP or COP (Step S2) arranged to be opposed to each of different parts of the content filling station 6 in the chamber 21. The injection nozzles 45 are fixed to the interior of the chamber 21 at predetermined locations.

Reference numeral 46 denotes a reservoir tank, which is a supply source of a predetermined working fluid, such as a liquid chemical agent such as an alkali cleaner, a peracetic acid cleaner or a hydrogen peroxide solution, or aseptic water. The reservoir tank 46 is provided for each of different liquid chemical agents such as a hydrogen peroxide solution or aseptic water, although only one reservoir tank 46 is shown for convenience of drawing. Reference numerals 47 and 48 denote supply pipes extending from each reservoir tank 46 to the injection nozzle 32 described above. Each of the supply pipes 47 and 48 is provided with a pump 49.

Alternatively, the pumps 39, 49 and the like may be omitted, and the reservoir tanks 38 and 46 may be located at high elevations so that the cleaner, liquid chemical agent or the like can be supplied into the chamber 21 or the like under hydrostatic pressure.

When the CIP (Step S1) of the interior of the drink supply piping 34 in the content filling station 6 is completed, and the coupling 44 is disconnected, the clutch described above is connected, so that the wheel 9 is allowed to rotate in association with the other wheels 13, 17 and the like. Alternatively, the wheel 9 is allowed to rotate by being driven by the dedicated servo motor for the wheel 9.

When the wheel 9 starts rotating, the SOP or COP (Step S2) in the chamber 21 is started.

The SOP or COP (Step S2) of the content filling station 6 in the chamber 21 is performed by blasting the sterilizer such as a peracetic acid solution from the injection nozzles 45 to the exterior of the content filling station 6 and then blasting aseptic water from the same injection nozzles 45. The sterilizer blasted to the content filling station 6 sterilizes the outer surface of the content filling station 6, and the aseptic water subsequently blasted washes the remainder of the drink in the previous filling operation and the sterilizer such as peracetic acid from the surface of the content filling station 6.

During the SOP or COP (Step S2), the filling nozzles 32 or the like rotate with the wheel 9. Since the working fluid is blasted to the rotating content filling station 6, foreign matters or the like are efficiently washed from the outer surface of the filling nozzles 32, which have a particularly complicated shape and structure, and the surface of the filling nozzles 32 is efficiently sterilized.

In the period from the start of the CIP (Step S1) to the end of the SIP (Step S3), aseptic air, desirably aseptic hot air, is constantly blasted from the aseptic air supply source described above to the content filling station 6 in the chamber 21. This ensures that the atmosphere in the chamber 21 is kept at a positive pressure, and the outside air containing bacteria, dust or the like is prevented from entering the chamber 21. Furthermore, the aseptic air also flows to the container sealing station 7 in the same chamber 21 and the container sterilizing station 5 in the chamber 20, so that the outside air is also prevented from entering the container sealing station 7 and the like.

The decontaminating apparatuses for the container molding station 4, the container sealing station 7, the container sterilizing station 5 and the cap sterilizing station 53 will be now described. In order to perform one or both of the SOP and COP (Steps S4, S5, S6, S7) of the stations 4, 7, 5 and 53, as shown in FIG. 1, injections nozzles 57 having the same structure as the injection nozzles 45 are arranged at locations in the chamber 19 so as to be opposed to the container molding station 4, injection nozzles 52 having the same structures as the injection nozzles 45 are arranged at locations in the chamber 21 so as to be opposed to the container sealing station 7, injection nozzles 50 having the same structures as the injection nozzles 45 are arranged at locations in the chamber 20 so as to be opposed to the container sterilizing station 5, and injection nozzles 54 having the same structure as the injection nozzles 45 are arranged at locations in the chamber 56 so as to be opposed to the cap sterilizing station 53.

Supply pipes (not shown) extend from the reservoir tank 46 to the injection nozzles 57, 52, 50 and 54, and the supply pipes are also provided with a pump (not shown) that feeds a liquid chemical agent or the like to these pipes under pressure.

As shown in FIG. 4, the controlling portion (not shown) is programmed to perform the SOP or COP (Steps S4, S5, S6, S7) of the container molding station 4, the container sealing station 7, the container sterilizing station 5 and the cap sterilizing station 53 in the period from the start of the CIP (Step S1) to the end of the SIP (Step S3) of the content filling station 6. In addition, the controlling portion is programmed to perform two types of SOP (Steps S4, S5, S6, S7) on each station.

As shown in FIG. 4, the SOP performed first (Step S4) is performed in synchronization with the CIP (Step S1) of the content filling station 6 and performed simultaneously for all of the container molding station 4, the container sealing station 7, the container sterilizing station 5 and the cap sterilizing station 53.

The SOP or COP (Step S4) is different from the SOP or COP (Step S2) of the content filling station 6 and is performed by spraying a hydrogen peroxide solution from the injection nozzles 57, 50, 52 and 54 to the outer surface of the container molding station 4, the container sterilizing station 5, the container sealing station 7 and the cap sterilizing station 53. In the SOP or COP (Step S4), the hydrogen peroxide solution may be sprayed from the injection nozzles 45 to the content filling station 6 at the same time and dried and vaporized by aseptic hot air.

In the SOP or COP (Step S4), the hydrogen peroxide solution serving as a working fluid is blasted to each of the stations 4, 5, 7 and 53 while the wheels 10, 12, 13 and the like other than the wheel 9 are rotating, so that the sterilization effect of the stations 4, 5, 7 and 53 is improved.

That is, in the CIP (Step S1), although the clutch is disconnected to stop the wheel 9 of the content filling station 6 as described above, the other wheels 17 and the like can rotate. In the alternative case, even if the dedicated servo motor for the wheel 9 of the content filling station 6 is stopped, the other wheels 17 and the like can rotate by being driven by the respective dedicated servo motors. Thus, even if the wheel 9 of the content filling station 6 is stopped when the CIP (Step S1) of the content filling station 6 is performed, the other wheels 17 and the like of the other stations such as the container sterilizing station 5 can rotate, so that the SOP or COP (Step S4) of the outer surface of the stations other than the content filling station 6, that is, the container molding station 4, the container sterilizing station 5, the container sealing station 7 and the cap sterilizing station 53, can be effectively performed.

The sterilizer used for the SOP effectively contains 1% or more of hydrogen peroxide. Alternatively, the sterilizer may contain one or more of ethanol, peracetic acid, acetic acid, octanoic acid, peroxyoctanoic acid, ozone, chlorine dioxide, chlorinated alkali and sodium hypochlorite or a mixture thereof. The sterilizer may be gas or mist, rather than liquid.

When the SOP or COP (Step S4) is performed, if aseptic hot air has been blasted into the chambers 19, 20, 21 and 56 before spraying the hydrogen peroxide solution, the temperature of the atmosphere in the chambers 19, 20, 21 and 56 increases, so that the hydrogen peroxide is activated, and the effect of sterilization by the SOP or COP (Step S4) is improved. After spraying of the hydrogen peroxide solution, the aseptic hot air promotes drying and removal of any excessive hydrogen peroxide solution.

The SOP or COP (Steps S5, S6, S7) that follows the SOP or COP (Step S4) described above is different from the SOP or COP (Step S4) and is the same as the SOP or COP (Step S2) of the content filling station 6. The SOP or COP (Steps S5, S6, S7) is performed stepwise for the container sealing station 7, the container sterilizing station 5 and the cap sterilizing station 53 in the period from the SOP or COP (Step S2) of the content filling station 6 to the end of the SIP (Step S3).

In the different SOP or COP (Steps S5, S6, S7), a peracetic acid solution is first blasted from the injection nozzles 52, 50 and 54 to the container sealing station 7, the container sterilizing station 5 and the cap sterilizing station 53 to sterilize the outer surface of the stations 7, 5 and 53, and aseptic water is then blasted to the stations to wash the remainder of the drink in the previous filling, the excessive peracetic acid solution or the like from the surface of the stations 7, 5 and 53.

When the SIP (Step S3) of the content filling station 6 is performed, although the wheel 9 of the content filling station 6 is stopped, the other wheels 12, 13 and the like of the container sealing station 7, the container sterilizing station 5 and the cap sterilizing station 53 can rotate. Thus, when the SOP or COP (Steps S5, S6, S7) of the container sealing station 7, the container sterilizing station 5 and the cap sterilizing station 53 in the chambers 20, 21 and 56 is performed in the period from the SOP or COP (Step S2) to the SIP (Step S3) of the content filling station 6, the cleaning effect of the stations 7, 5 and 53 by blasting of peracetic acid or aseptic water as a working fluid is improved.

When the SOP or COP (Steps S5, S6, S7) is performed, the aseptic hot air is blasted into the chambers 21, 20 and 56.

According to the first embodiment, as shown in FIG. 4, the SOP or COP (Steps S2, S5, S6, S7) using peracetic acid and aseptic water of the content filling station 6, the container sealing station 7, the container sterilizing station 5 and the cap sterilizing station 53 is performed stepwise in the period from the start of the SOP or COP (Step S2) to the end of the SIP (Step S3) of the content filling station 6, because it is difficult to supply the peracetic acid and aseptic water to all the stations at the same time.

In this process, the cleaning with the aseptic water in each preceding SOP or COP and the cleaning with the peracetic acid in the subsequent SOP or COP are preferably performed in a temporally overlapped manner. This is intended to prevent the peracetic acid supplied in each SOP or COP from adhering to a part where the peracetic acid in the preceding SOP or COP is being washed and removed.

When the SOP or COP (Steps S5, S6, S7) is performed, if the sterilizer or cleaner such as peracetic acid comes into contact with the filling valves 32, heat of the filling valves 32 is lost, and thus the filling valves 32 can be poorly sterilized. To avoid this, a partition wall that prevents the sterilizer or cleaner from flowing to the content filling station 6 is preferably provided between the content filling station 6 and the other stations. Alternatively, gas or mist of the sterilizer, rather than the sterilizing liquid, is preferably used as a sterilizer for the SOP or COP in the other chambers.

Next, operations of the aseptic filling apparatus described above and a method of decontaminating the aseptic filling apparatus will be described.

(1) First, a decontamination operation of the aseptic filling apparatus will be described with reference to the flowchart of FIG. 4.

When manufacture of the bottled drink is finished, and manufacture of another kind of bottled drink is started by changing the kind of drink, the CIP (Step S1), the SIP (Step S3) and the SOP or COP (Steps S2, S5, S6, S7) are performed on the aseptic filling apparatus.

In the period from the start of the CIP (Step S1) to the end of the SIP (Step S3), aseptic hot air is preferably constantly blasted to the content filling station 6 in the chamber 21. This ensures that the atmosphere in the chamber 21 is kept at a positive pressure, and the outside air containing bacteria, dust or the like is prevented from entering the chamber 21. The aseptic air also flows to the container sealing station 7 in the same chamber 21 and the container sterilizing station 5 in the chamber 20, so that contamination of the container sealing station 7 and the like is also prevented. Aseptic air is also supplied into the chamber 56 for the cap sterilizing station 53.

(2) Before starting the CIP (Step S1) of the content filling station 6, the clutch in the power transmission system of the aseptic filling apparatus is disconnected to stop rotation of only the wheel 9 of the content filling station 6, thereby stopping rotation of the filling nozzles 32. In addition, the surge tank 33 is emptied.

(3) As shown in the right half of FIG. 3, the nozzle mouth 32a of the filling nozzle 32 is then closed by the cup 42. In addition, the coupling 44 is connected. In this way, a circulation path for flowing a predetermined working fluid for the CIP (Step S1) such as a cleaning liquid or sterilizing liquid is formed.

(4) The CIP (Step S1) is started, and a predetermined working fluid such as an alkali cleaner or water is fed from the reservoir tank 38 by the pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean the interior of the drink supply piping 34 including the interior of the filling nozzles 32.

(5) After the CIP (Step S1) is completed, the clutch in the power transmission system of the aseptic filling apparatus is connected, so that the wheel 9 of the content filling station 6 starts rotating along with the other wheels, and thus the filling nozzles 32 also start rotating.

In response to this, the SOP or COP (Step S2) of the content filling station 6 is started, and a predetermined working fluid such a liquid chemical agent or aseptic water is injected from the injection nozzles 45 to the exterior of the content filling station 6 in a predetermined order. Since the working fluid is blasted to the rotating filling nozzles 32 and the like, the outer surface of the filling nozzles 32 and the like is efficiently cleaned and sterilized.

The SOP or COP of Step S2 may be a process of deactivating bacteria by using warm water or the like of a temperature equal to or higher than 60° C. and lower than 100° C. instead of the sterilizer.

In the SOP or COP (Step S2) according to the first embodiment, the peracetic acid solution as a sterilizer is first blasted from the injection nozzles 45 to the content filling station 6 to sterilize the outer surface of the content filling station 6, and aseptic water is then blasted to wash any excessive peracetic acid as a sterilizer or dirt from the surface of the content filling station 6.

(6) When the SOP or COP (Step S2) of the content filling station 6 is completed, the clutch in the power transmission system of the aseptic filling apparatus is disconnected to stop rotation of only the wheel 9 in the content filling station 6, thereby stopping rotation of the filling nozzles 32.

(7) As shown in the right half of FIG. 3, the nozzle mouth 32a of the filling nozzle 32 is then closed by the cup 42. In addition, the coupling 44 is connected. In this way, a circulation path for flowing a predetermined working fluid for the SIP (Step S3) such as a cleaning liquid or sterilizing liquid is formed.

(8) The SIP (Step S3) is started, and a predetermined working fluid such as hot water or heated vapor is fed from a supply source of hot water or the like (not shown) to the circulation path described above for a predetermined time. In this way, the interior of the drink supply piping 34 including the filling nozzles 32 is sterilized.

(9) When the CIP (Step S1) of the drink supply piping 34 of the content filling station 6 is performed, the SOP or COP (Step S5) is performed in parallel therewith on (i) the outer surface of various kinds of equipment in the container molding station 4 in the chamber 19, (ii) the outer surface of various kinds of equipment in the container sterilizing station 5 in the chamber 20, (iii) the outer surface of various kinds of equipment in the container sealing station 7 in the chamber 21, and (iv) the outer surface of various kinds of equipment in the chamber 56 for the cap sterilizing station 53.

In this process, the wheel 9 of the content filling station 6 is stopped, while the equipment, such as the wheels 10, 12, 13, 17 and 18, in the container molding station 4, the container sterilizing station 5, the container sealing station 7 and the cap sterilizing station 53 are being driven.

The SOP or COP (Step S4) is different from the SOP or COP (Step S2) of the content filling station 6 in that a hydrogen peroxide solution is blasted from the injection nozzles 57, 50, 52 and 54 to the outer surface of the container molding station 4, the container sterilizing station 5, the container sealing station 7 and the cap sterilizing station 53.

In this process, since the container molding station 4, the container sterilizing station 5, the container sealing station 7 and the cap sterilizing station 53 are being driven, the hydrogen peroxide solution as a working fluid spreads into every corner of the various kinds of equipment thereof to improve the cleaning effect and the sterilization effect.

In the SOP or COP (Step S4), the hydrogen peroxide solution may also be sprayed to the content filling station 6 at rest to perform the SOP or COP (Step S4) of the content filling station 6 in parallel with the CIP (Step S1) thereof.

When the SOP or COP (Step S4) is performed, the temperature of the atmosphere in the chamber 20 is raised by the aseptic hot air blasted into the chamber 21 described above. As a result, the hydrogen peroxide is activated, the sterilization effect of the SOP or COP (Step S4) is improved, and any excessive hydrogen peroxide solution is dried and removed by the aseptic hot air after spraying of the hydrogen peroxide solution.

(10) The same SOP or COP (Steps S5, S6, S7) as the SOP or COP (Step S2) of the content filling station is performed stepwise on the container sterilizing station 5, the container sealing station 7 and the cap sterilizing station 53 in the period from the start of the SOP or COP (Step S2) to the end of the SIP (Step S3) of the content filling station.

(11) Steps S5, S6 and S7 can be performed in any order.

Supposing that Step S5 is first performed, a peracetic acid solution is sprayed from the injection nozzles 52 to the container sealing station 7 during spraying of the aseptic water in Step S2.

In this way, the outer surface of the container sealing station 7 is sterilized by the peracetic acid. In addition, since the peracetic acid is blasted to the outer surface of the container sealing station 7 while the aseptic water is being blasted to the content filling station 6, the peracetic acid can be prevented from adhering to the outer surface of the content filling station 6.

After the peracetic acid is sprayed to the outer surface of the container sealing station 7 in Step S5, aseptic water is sprayed. In this way, the peracetic acid is washed from the outer surface of the container sealing station 7, and the SOP or COP of Step S5 is completed.

During Step S5, since the container sealing station 7 is being driven, and the various wheels other than the wheel 9 are rotating, the peracetic acid and the aseptic water as working fluids spread into every corner of the various kinds of equipment of the container sealing station 7 to improve the cleaning effect and the sterilization effect.

(12) Step S6 is then performed.

In Step S6, blasting of the peracetic acid solution from the nozzles 50 to the container sterilizing station 5 is performed in synchronization with blasting of the aseptic water in Step S5, and when the blasting of the aseptic water in Step S5 is completed, blasting of the aseptic water from the nozzles 50 to the container sterilizing station 5 is performed.

Since the wheel 12 or the like of the container sterilizing station 5 is being driven when the peracetic acid solution and the aseptic water are blasted, the effect of cleaning and sterilization of the outer surface of the container sterilizing station 5 is improved.

Since the SOP or COP (Step S6) of the container sterilizing station 5 is performed in parallel with the SIP (Step S3) of the drink supply piping 34, the downtime of the aseptic filling apparatus is reduced, and the productivity of the bottled drink is improved.

(13) Step S7 is then performed.

In Step S7, blasting of the peracetic acid solution from the nozzles 54 to the cap sterilizing station 53 is performed in synchronization with blasting of the aseptic water in Step S6, and when the blasting of the aseptic water in Step S6 is completed, blasting of the aseptic water from the nozzles 54 to the cap sterilizing station 53 is performed.

Since the wheel or the like of the cap sterilizing station 53 is being driven when the peracetic acid solution and the aseptic water are blasted, the effect of cleaning and sterilization of the outer surface of the cap sterilizing station 53 is improved.

Since the SOP or COP (Step S7) of the cap sterilizing station 53 is performed in parallel with the SIP (Step S3), the downtime of the aseptic filling apparatus is reduced, and the productivity of the bottled drink is improved.

(14) In this way, the aseptic filling apparatus is decontaminated by performing the CIP (Step S1), the SIP (Step S3) and the SOP or COP (Steps S2, S4, S5, S6, S7) of the parts of the aseptic filling apparatus where contamination is particularly unwanted.

In addition, the aseptic air continues being blasted into the chamber 21 to keep the surroundings of the content filling station 7 at a positive pressure. The aseptic air further flows to the container molding station 4, the container sterilizing station 5 and the container sealing station 7. Thus, the aseptic condition in the chambers 19, 20 and 21 is maintained.

For the cap sterilizing station 53, the aseptic condition of the atmosphere in the chamber 56 is maintained by blasting aseptic air into the chamber 56 from another system.

As shown in FIG. 4, the time required to decontaminate the aseptic filling apparatus by the CIP (Step S1), the SIP (Step S3) and the SOP or COP (Steps S2, S4, S5, S6, S7) described in (1) to (13) above is about three hours. The time required for decontamination of conventional aseptic filling apparatuses is about six hours as shown in FIG. 6, and it can be seen that the downtime is reduced to about half according to the present invention.

(15) After the CIP (Step S1), the SIP (Step S3) and the SOP or COP (Steps S2, S4, S5, S6, S7) described above are completed, manufacture of another kind of bottled drink is started.

Manufacture of another kind of bottled drink will be described. Referring to FIG. 1, first, the preform 1 is introduced into the heating furnace by the shooter 22 and the wheel 23, and conveyed by the endless chain 24 in the heating furnace.

The preform 1 is heated to a temperature range suitable for molding by the heater 25 while the preform 1 is conveyed by the endless chain 24 in the heating furnace.

(16) The heated preform 1 is put in the molding die 8 rotating around the wheel 10, and the molding die 8 is closed. An extension rod (not shown) is lowered into the preform 1 until the extension rod abuts against the bottom of the preform 1, and starts expanding the preform 1. In addition, blow molding air is blasted to expand the preform 1 in the molding die 8 into the bottle 3. Once the molding of the bottle 3 in the molding die 8 is completed, the molding die 8 is opened, and the finished bottle 3 is removed from the molding die 8 by a gripper (not shown) disposed around the wheel 11.

(17) The bottle 3 conveyed from the wheel 11 travels around the wheel 12 in the chamber 20 having been subjected to the SOP or COP (Step S6), and meanwhile, a mist of the sterilizer is blasted to the bottle 3 from the sterilizer spraying nozzle 27 of the container sterilizing station 5. Thus, a coating of the sterilizer is formed on the inner and outer surfaces of the bottle 3, and the inner and outer surfaces of the bottle 3 are sterilized.

After that, heated aseptic air is blasted to the bottle 3 from the air rinsing nozzle 28 of the container sterilizing station 5 while the bottle 3 is traveling around the wheel 13. Thus, the sterilizer on the inner and outer surfaces of the bottle 3 is activated to improve the sterilization effect, and any excessive sterilizer is removed.

(18) The sterilized bottle 3 travels in the chamber 21 by being passed between the wheels 14, 15, 9, 16, 17 and 18 in the bottle conveying path. The SOP or COP (Step S2) in the chamber 21 has already been completed, and the aseptic air is constantly being blasted into the chamber 21.

(19) While the bottle 3 is traveling around the wheel 9, the bottle 3 is filled with a content, such as a drink, from the drink supply piping 34.

The interior of the drink supply piping 34 has already been subjected to cleaning by CIP (Step S1) and sterilization by SIP (Step S3) and decontaminated.

The bottle 3 is filled with a content, such as a drink, from the filling nozzle 32 through the decontaminated drink supply piping 34 of the content filling station 6.

The content is previously prepared in the preparation apparatus, sterilized and stored in the serve tank 33.

(20) The bottle 3 filled with the drink is passed from the gripper 36 at the wheel 9 to a gripper at the downstream wheel 16, and then to a gripper at the further downstream wheel 17, the mouth portion 3a of the bottle 3 is closed by the sterilized cap 51 in the container sealing station 7, and then the bottle 3 is ejected out of the chamber 21.

The cap 51 is previously sterilized in the cap sterilizing station 53 before the cap 51 is supplied to the container sealing station 7. The interior of the cap sterilizing station 53 has already been decontaminated by cleaning and sterilization by the SOP or COP (Steps S4, S7) described above.

Manufacture of another kind of aseptic bottled drink is performed as described above.

Second Embodiment

Figure 5:
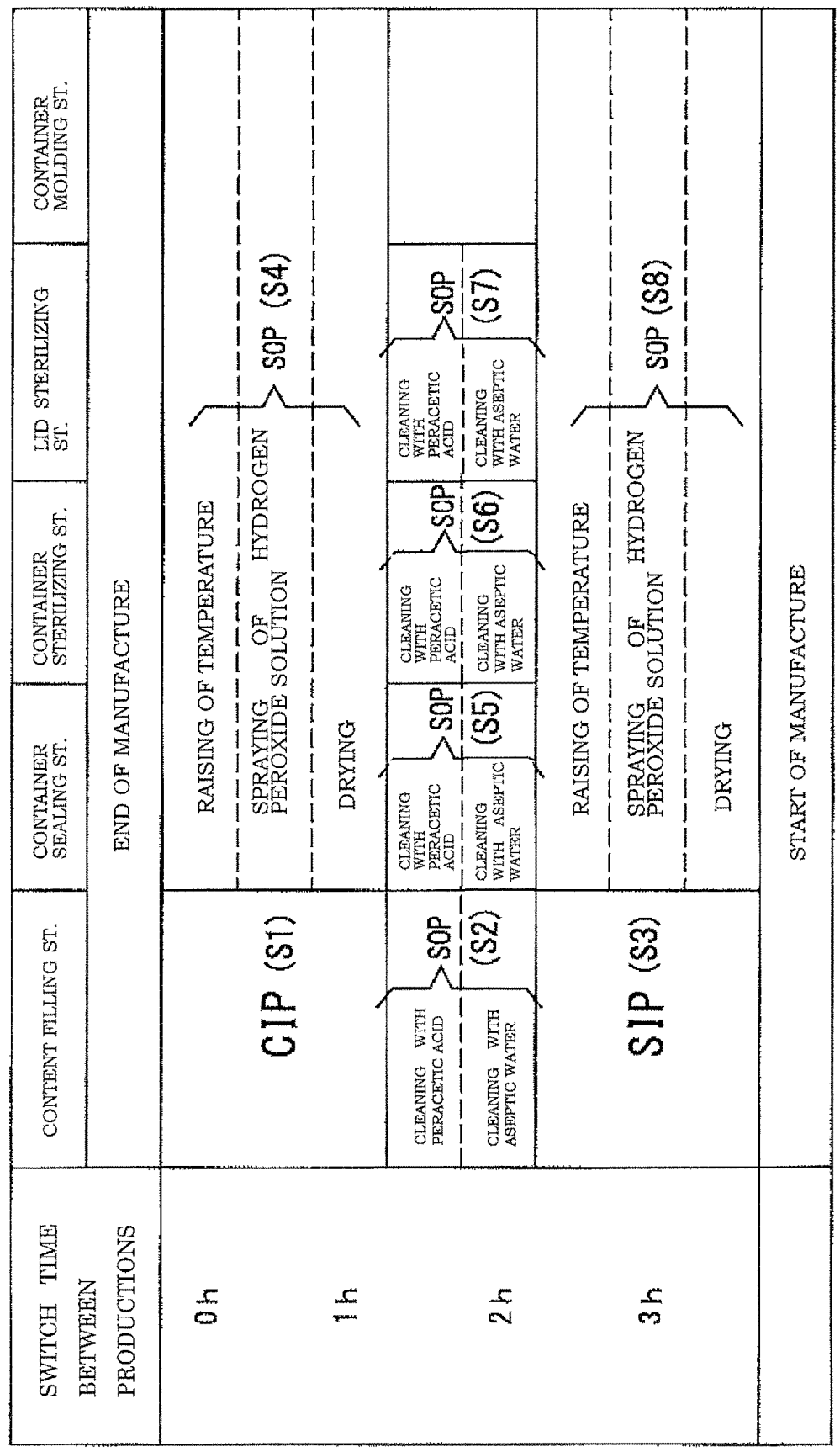
FIG. 5 is a flowchart showing another decontaminating method.

As shown in FIG. 5, according to a second embodiment, although the CIP (Step S1), SIP (Step S3) and the SOP or COP (steps S2, S5, S6, S7) achieved by spraying a hydrogen peroxide solution are performed as in the first embodiment, the SOP or COP (Steps S2, S5, S6, S7) achieved by blasting a peracetic acid solution and aseptic water is simultaneously performed on the content filling station 6, the container sealing station 7, the container sterilizing station 5 and the cap sterilizing station 53.

Since the SOP or COP (Steps S5, S6, S7) of the container sterilizing station 5, the container sealing station 7 and the cap sterilizing station 53 is performed in parallel with the SOP or COP (Step S2) of the content filling station 6 in this way, the downtime of the aseptic filling apparatus is further reduced, and the productivity of the bottled drink is further improved.

In addition, when the CIP (Step S1) of the content filling station 6 is performed, the SOP or COP (Step S4) using hydrogen peroxide of the other stations such as the container sealing station 7 is performed in parallel therewith. In this process, the wheels 17 and the like of the other stations such as the container sealing station 7 are rotating, so that the sterilization effect of the other stations such as the container sealing station 7 is improved.

Furthermore, when the SIP (Step S3) of the content filling station 6 is performed, the SOP or COP (Step S4) using hydrogen peroxide of the other stations being driven, such as the container sealing station 7, is performed in parallel therewith. Thus, the sterilization effect of the other stations such as the container sealing station 7 is further improved.

Third Embodiment

Figure 7:
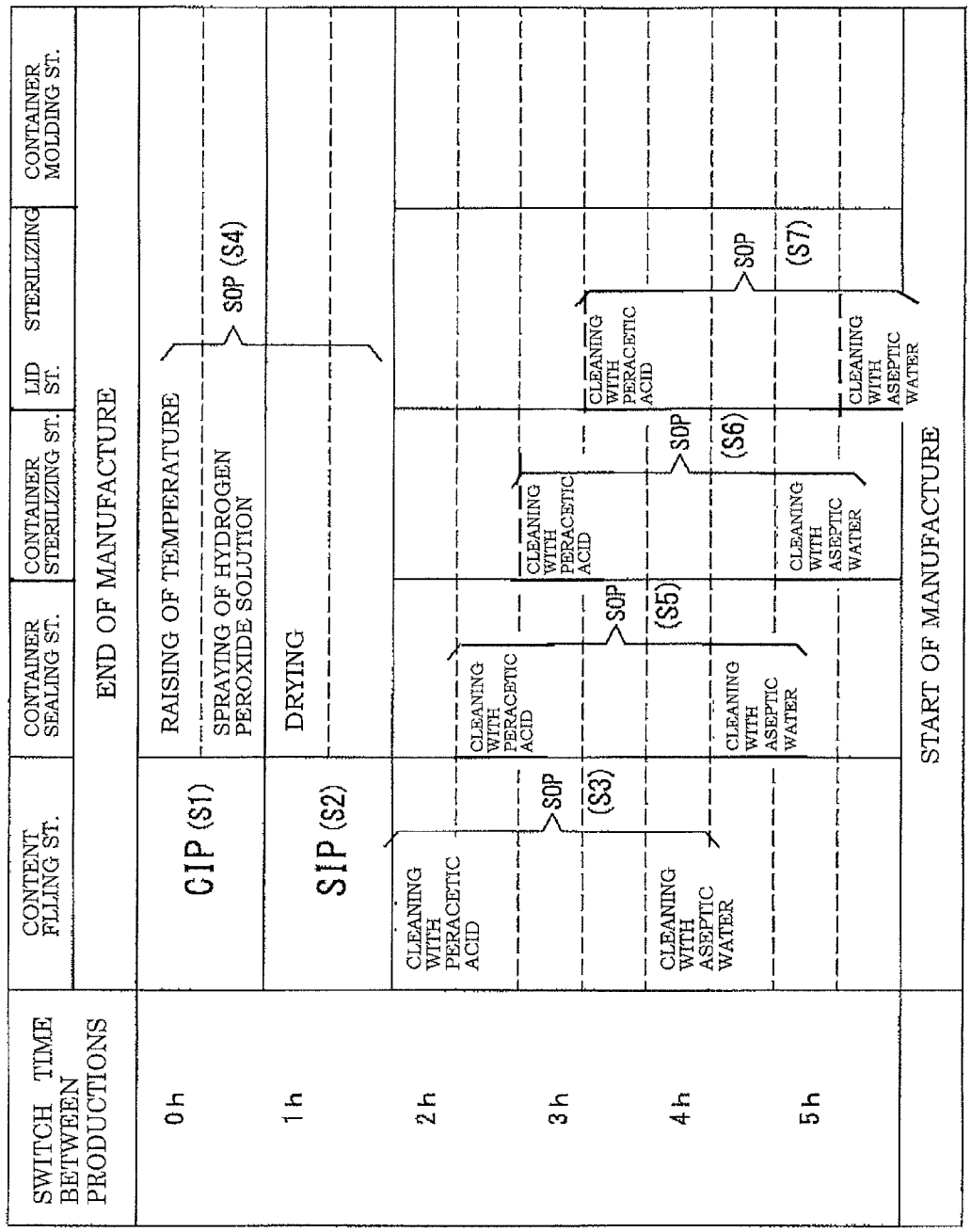
FIG. 7 is a flowchart showing a decontaminating method for the aseptic filling apparatus.

According to a third embodiment, as shown in FIG. 7, the controlling portion (not shown) is programmed to successively perform the CIP, the SIP and the SOP or COP for the content filling station 6.

First, before starting the CIP (Step S1) of the content filling station 6, the clutch in the power transmission system of the aseptic filling apparatus is disconnected to stop rotation of only the wheel 9 in the content filling station 6, thereby stopping rotation of the filling nozzles 32.

As shown in the right half of FIG. 3, the nozzle mouth 32a of the filling nozzle 32 is then closed by the cup 42. In addition, the coupling 44 is connected. In this way, a circulation path for flowing a predetermined working fluid for the CIP such as a cleaning liquid or sterilizing liquid is formed.

The CIP (Step S1) is then started, and a predetermined working fluid such as an alkali cleaner or water is fed from the reservoir tank 38 by the pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean the interior of the drink supply piping 34 including the interior of the filling nozzles 32.

Figure 8:
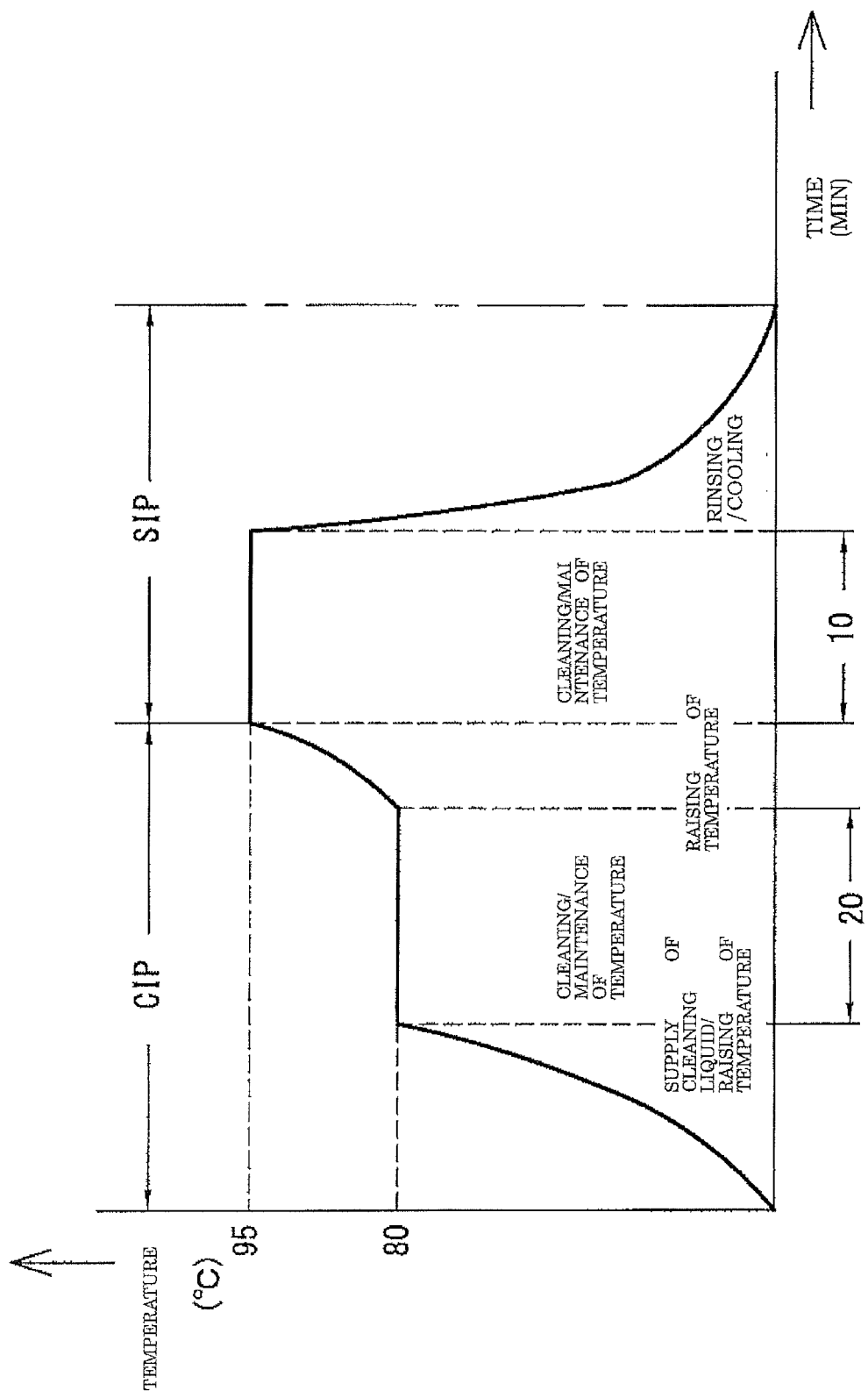
FIG. 8 is a diagram for illustrating a process of shifting from a CIP to a SIP of the interior of a drink supply piping in FIG. 7.

As shown in FIG. 8, the working fluid such as the cleaning liquid circulates in the drink supply piping 34 for 20 minutes, for example, while the working fluid is heated to about 80° C., for example. In a middle of the CIP, for example, in a final stage of the CIP, the temperature of the working fluid is raised to a sterilization temperature required for the subsequent SIP, such as 95° C. The operating temperature range is preferably from 80° C. to 99° C. The cleaning liquid used from the middle of the CIP is preferably water, because the cleaning liquid is used also for rinsing of the cleaning liquid. The temperature of the working fluid may be raised to the sterilization temperature at the start of the CIP.

Following the CIP (Step S1) is completed, the SIP (Step S2) of the content filling station 6 is performed with rotation of the wheel 9 of the content filling station 6 kept stopped.

The SIP is performed by passing the working fluid such as water used in the CIP described above through the drink supply piping 34 while keeping the temperature of the working fluid at a temperature required for sterilization. As shown in FIG. 8, the working fluid circulates in the drink supply piping 34 for 10 minutes, for example, while the working fluid is heated to about 95° C., for example. Thus, the interior of the drink supply piping 34 is sterilized. In the case of SIP serving as rinsing, hot water does not circulate but is fed in one direction.

After the interior of the drink supply piping 34 is sterilized, as shown in FIG. 8, the water passing through the piping is gradually cooled to room temperature.

As described above, since the temperature of the cleaning liquid is raised to a temperature required for the SIP (Step S2) following the CIP (Step S1) in an early or middle stage of the CIP (Step S1), so that the SIP (Step S2) can be started immediately after the CIP (Step S1), the downtime can be reduced.

After the SIP (Step S2) is completed, the SOP or COP (Step S3) of the content filling station 6 is performed.

In FIG. 3, reference numeral 45 denotes an injection nozzle for the SOP or COP (Step S3) arranged to be opposed to each of different parts of the content filling station 6 in the chamber 21. The injection nozzles 45 are fixed to the interior of the chamber 21 at predetermined locations.

Reference numeral 46 denotes a reservoir tank, which is a supply source of a predetermined working fluid, such as a liquid chemical agent such as an alkali cleaning liquid, a peracetic acid cleaning liquid or a hydrogen peroxide solution, or aseptic water. The reservoir tank 46 is provided for each of different liquid chemical agents such as a hydrogen peroxide solution or aseptic water, although only one reservoir tank 46 is shown for convenience of drawing. Reference numerals 47 and 48 denote supply pipes extending from each reservoir tank 46 to the injection nozzle 32 described above. Each of the supply pipes 47 and 48 is provided with a pump 49.

Alternatively, the pumps 39, 49 and the like may be omitted, and the reservoir tanks 38 and 46 may be located at high elevations so that the cleaning liquid, liquid chemical agent or the like can be supplied into the chamber 21 or the like under hydrostatic pressure.

When the SIP (Step S2) of the interior of the drink supply piping 34 in the content filling station 6 is completed, and the coupling 44 is disconnected, the clutch described above is connected, so that the wheel 9 is allowed to rotate in association with the other wheels 13, 17 and the like. Alternatively, the wheel 9 is allowed to rotate by being driven by the dedicated servo motor for the wheel 9.

When the wheel 9 starts rotating, the SOP or COP (Step S3) in the chamber 21 is started at the same time.

The SOP or COP (Step S3) of the content filling station 6 in the chamber 21 is performed by blasting the sterilizer such as a peracetic acid solution from the injection nozzles 45 to the exterior of the content filling station 6 and then blasting aseptic water from the same injection nozzles 45. The sterilizer blasted to the content filling station 6 sterilizes the outer surface of the content filling station 6, and the aseptic water subsequently blasted washes the remainder of the drink in the previous filling operation and the sterilizer such as peracetic acid from the surface of the content filling station 6.

During the SOP or COP (Step S3), the filling nozzles 32 or the like rotate with the wheel 9. Since the working fluid is blasted to the rotating content filling station 6, foreign matters or the like are efficiently washed from the outer surface of the filling nozzles 32, which have a particularly complicated shape and structure, and the surface of the filling nozzles 32 is efficiently sterilized.

In the period from the start of the CIP (Step S1) to the end of the last SOP or COP (Step S7) described later, aseptic air, desirably aseptic hot air, supplied from the aseptic air supply source described above is constantly blasted to the content filling station 6 in the chamber 21. This ensures that the atmosphere in the chamber 21 is kept at a positive pressure, and the outside air containing bacteria, dust or the like is prevented from entering the chamber 21. Furthermore, the aseptic air also flows to the container sealing station 7 in the same chamber 21 and the container sterilizing station 5 in the chamber 20, so that the outside air is also prevented from entering the container sealing station 7 and the like.

The decontaminating apparatuses for the container molding station 4, the container sealing station 7, the container sterilizing station 5 and the cap sterilizing station 53 will be now described. In order to perform one or both of the SOP and COP (Steps S4, S5, S6, S7) of the stations 4, 7, 5 and 53, as shown in FIG. 1, injections nozzles 57 having the same structure as the injection nozzles 45 are arranged at locations in the chamber 19 so as to be opposed to the container molding station 4, injection nozzles 52 having the same structures as the injection nozzles 45 are arranged at locations in the chamber 21 so as to be opposed to the container sealing station 7, injection nozzles 50 having the same structures as the injection nozzles 45 are arranged at locations in the chamber 20 so as to be opposed to the container sterilizing station 5, and injection nozzles 54 having the same structure as the injection nozzles 45 are arranged at locations in the chamber 56 so as to be opposed to the cap sterilizing station 53.

Supply pipes (not shown) extend from the reservoir tank 46 to the injection nozzles 57, 52, 50 and 54, and the supply pipes are also provided with a pump (not shown) that feeds a liquid chemical agent or the like to these pipes under pressure.

As shown in FIG. 7, the controlling portion (not shown) is programmed to perform the SOP or COP (Steps S4, S5, S6, S7) of the container molding station 4, the container sealing station 7, the container sterilizing station 5 and the cap sterilizing station 53 from the start of the CIP (Step S1) of the content filling station 6. In addition, the controlling portion is programmed to perform two types of SOP (Steps S4, S5, S6, S7) on each station.

As shown in FIG. 7, the SOP performed first (Step S4) is performed in synchronization with one or both of the CIP (Step S1) and the SIP (Step S2) of the content filling station 6 and performed simultaneously for all of the container molding station 4, the container sealing station 7, the container sterilizing station 5 and the cap sterilizing station 53.

The SOP or COP (Step S4) is different from the SOP or COP (Step S3) of the content filling station 6 and is performed by spraying a hydrogen peroxide solution from the injection nozzles 57, 50, 52 and 54 to the outer surface of the container molding station 4, the container sterilizing station 5, the container sealing station 7 and the cap sterilizing station 53. In the SOP or COP (Step S4), the hydrogen peroxide solution may be sprayed from the injection nozzles 45 to the content filling station 6 at the same time and dried and vaporized by aseptic hot air.

In the SOP or COP (Step S4), the hydrogen peroxide solution serving as a working fluid is blasted to each of the stations 4, 5, 7 and 53 while the wheels 10, 12, 13 and the like other than the wheel 9 are rotating, so that the sterilization effect of the stations 4, 5, 7 and 53 is improved.

That is, in the CIP (Step S1), although the clutch is disconnected to stop the wheel 9 of the content filling station 6 as described above, the other wheels 17 and the like can rotate. In the alternative case, even if the dedicated servo motor for the wheel 9 of the content filling station 6 is stopped, the other wheels 17 and the like can rotate by being driven by the respective dedicated servo motors. Thus, even if the wheel 9 of the content filling station 6 is stopped when the CIP (Step S1) of the content filling station 6 is performed, the other wheels 17 of the other stations such as the container sterilizing station 5 can rotate, so that the SOP or COP (Step S4) of the outer surface of the stations other than the content filling station 6, that is, the container molding station 4, the container sterilizing station 5, the container sealing station 7 and the cap sterilizing station 53, can be effectively performed.

The sterilizer used for the SOP effectively contains 1% by mass or more of hydrogen peroxide. Alternatively, the sterilizer may contain one or more of ethanol, peracetic acid, acetic acid, octanoic acid, peroxyoctanoic acid, ozone, chlorine dioxide, chlorinated alkali and sodium hypochlorite or a mixture thereof. The sterilizer may be gas or mist, rather than liquid.

When the SOP or COP (Step S4) is performed, if aseptic hot air has been blasted into the chambers 19, 20, 21 and 56 before spraying the hydrogen peroxide solution, the temperature of the atmosphere in the chambers 19, 20, 21 and 56 increases, so that the hydrogen peroxide is activated, and the effect of sterilization by the SOP or COP (Step S4) is improved. After spraying of the hydrogen peroxide solution, the aseptic hot air promotes drying and removal of any excessive hydrogen peroxide solution.

The SOP or COP (Steps S5, S6, S7) of the container sealing station 7, the container sterilizing station 5 and the cap sterilizing station 53 that follows the SIP (Step S2) described above is the same as the SOP or COP (Step S3) of the content filling station 6 and is performed stepwise along with the SOP or COP (Step S3) of the content filling station 6.

In the SOP or COP (Steps S5, S6, S7), a peracetic acid solution is first blasted stepwise from the injection nozzles 52, 50 and 54 to the container sealing station 7, the container sterilizing station 5 and the cap sterilizing station 53 to sterilize the outer surface of the stations 7, 5 and 53.

Once the injection of the hydrogen peroxide solution is completed, aseptic water is blasted stepwise to the outer surface of stations 7, 5 and 53. In this way, the remainder of the drink in the previous filling, the remainder of the peracetic acid solution and the like are washed from the surface of the stations 7, 5 and 53.

A shortage of supply of the sterilizer such as peracetic acid and the aseptic water can be prevented by injecting the hydrogen peroxide solution and the aseptic water stepwise in the SOP (or COP) as described above.

When the SOP (Step S3) of the content filling station 6 is performed, the wheel 9 of the content filling station 6 can rotate, and the other wheels 12, 13 and the like of the container sealing station 7, the container sterilizing station 5 and the cap sterilizing station 53 can also rotate. Thus, in the period from the SOP or COP (Step S3) of the content filling station 6 to the SOP (Step S7) of another station, the cleaning effect of the stations 6, 7, 5 and 53 by blasting of peracetic acid or aseptic water as a working fluid is improved.

When the SOP or COP (Steps S3, S5, S6, S7) is performed, the aseptic hot air is also blasted into the chambers 21, 20 and 56.

When the SOP or COP (Steps S5, S6, S7) is performed, if the sterilizer or cleaning liquid such as peracetic acid comes into contact with the filling valves 32, heat of the filling valves 32 is lost, and thus the filling valves 32 can be poorly sterilized. To avoid this, a partition wall that prevents the sterilizer or cleaning liquid from flowing to the content filling station 6 is preferably provided between the content filling station 6 and the other stations.

Alternatively, gas or mist of the sterilizer, rather than the sterilizing liquid, is preferably used as a sterilizer for the SOP or COP in the other chambers.

Next, operations of the aseptic filling apparatus described above and a method of decontaminating the aseptic filling apparatus will be described.

(1) First, a decontamination operation of the aseptic filling apparatus will be described with reference to the flowchart of FIG. 7.

When manufacture of the bottled drink is finished, and manufacture of another kind of bottled drink is started by changing the kind of drink, the CIP (Step S1), the SIP (Step S2) and the SOP or COP (Steps S3, S4, S5, S6, S7) are performed on the aseptic filling apparatus.

In the period from the start of the CIP (Step S1) to the end of the last SOP (Step S7), aseptic hot air is preferably constantly blasted to the content filling station 6 in the chamber 21. This ensures that the atmosphere in the chamber 21 is kept at a positive pressure, and the outside air containing bacteria, dust or the like is prevented from entering the chamber 21. The aseptic air also flows to the container sealing station 7 in the same chamber 21 and the container sterilizing station 5 in the chamber 20, so that contamination of the container sealing station 7 and the like is also prevented. Aseptic air is also supplied into the chamber 56 for the cap sterilizing station 53.

(2) Before starting the CIP (Step S1) of the content filling station 6, the clutch in the power transmission system of the aseptic filling apparatus is disconnected to stop rotation of only the wheel 9 of the content filling station 6, thereby stopping rotation of the filling nozzles 32. In addition, the surge tank 33 is emptied.

(3) As shown in the right half of FIG. 3, the nozzle mouth 32a of the filling nozzle 32 is closed by the cup 42. In addition, the coupling 44 is connected. In this way, a circulation path for flowing a predetermined working fluid for the CIP (Step S1) such as a cleaning liquid or sterilizing liquid is formed.

(4) The CIP (Step S1) is started, and a predetermined working fluid such as an alkali cleaning liquid or water is fed from the reservoir tank 38 by the pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean the interior of the drink supply piping 34 including the interior of the filling nozzles 32.

As shown in FIG. 8, from a middle of the CIP (Step S1), the water circulating in the drink supply piping 34 at a temperature of 80° C., for example, is heated to a temperature required for sterilization in the subsequent SIP (Step S2), such as 95° C. This is the end of the CIP (Step S1).

(5) After the CIP (Step S1) is completed, the SIP (Step S2) of the content filling station 6 is performed while rotation of the wheel 9 in the content filling station 6 is kept stopped. The SIP (Step S2) is performed by passing the hot water at 95° C. described above through the drink supply piping 34. The hot water passing through the drink supply piping 34 sterilizes the interior of the drink supply piping 34 including the filling nozzles 32 and the like and, at the same time, removes any remaining cleaning liquid or waste liquid in the CIP (Step S1) from the interior of the drink supply piping 34. Removal of the waste liquid or the like from the interior of the drink supply piping 34 is achieved by collecting the waste liquid or the like in the reservoir tank 38 and then drawing the waste liquid from the reservoir tank 38, for example.

Figure 12:
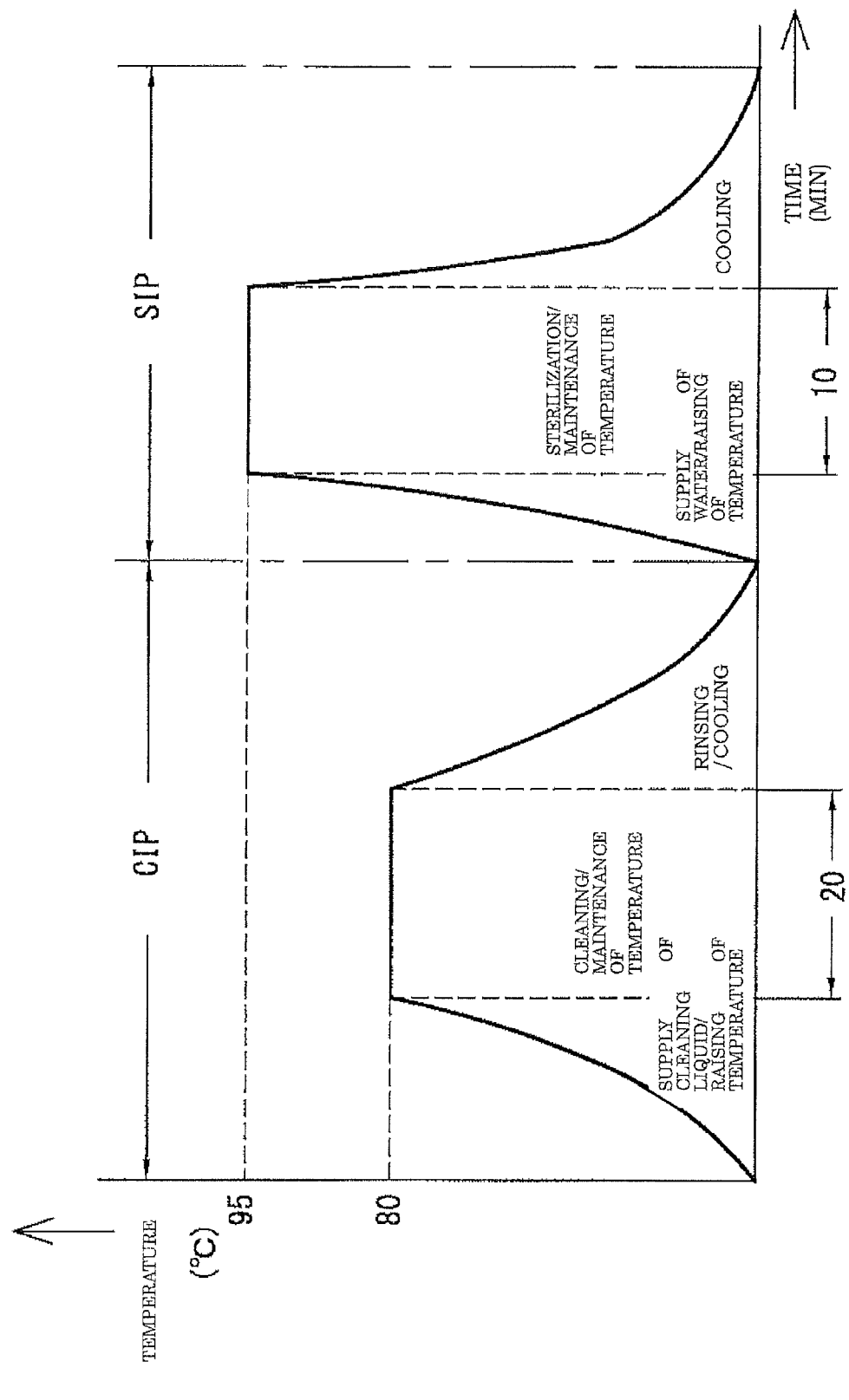
FIG. 12 is a diagram for illustrating a process of shifting from the CIP to the SIP of the interior of the drink supply piping in FIG. 11.
Figure 13:
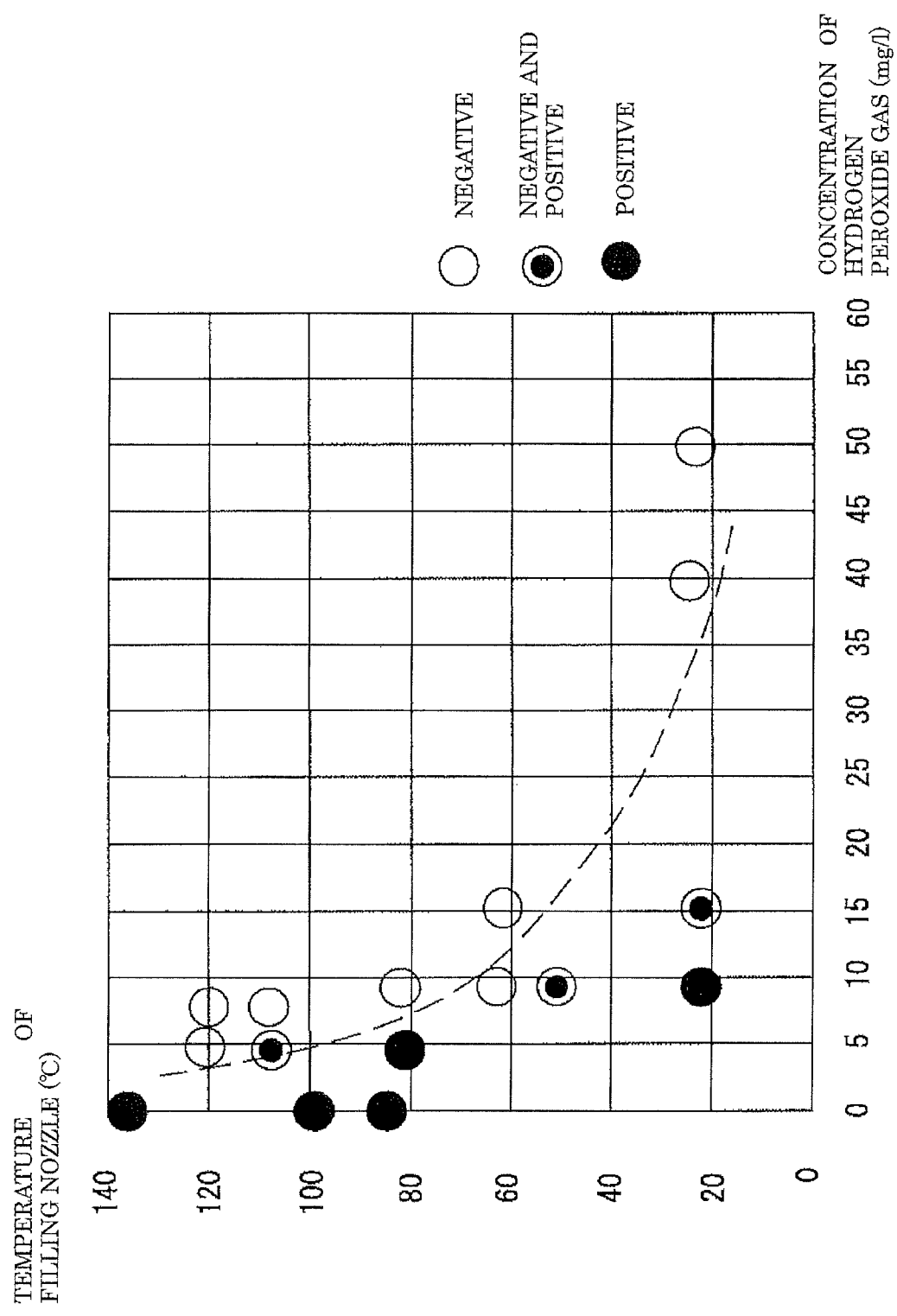
FIG. 13 is a graph showing a relationship between the temperature of a filling nozzle and a hydrogen peroxide gas concentration in sterilization of an outer surface of the filling nozzle.

As described above, since the SIP (Step S2) is started immediately after the CIP (Step S1) by raising the temperature of the working fluid during the cleaning step using a chemical agent such as an alkali or the rinsing step using hot water after the cleaning with the chemical agent, the idle time between the end of filling with a drink and the start of filling with another drink is reduced, as is obvious from comparison between FIGS. 8 and 12.

Conditions of the temperature of the hot water used in the SIP (Step S2) and the duration of the SIP (Step S2) are determined based on the conditions required for sterilization of the content of the product. For example, in the case of a product having a pH lower than 4, the temperature is at least 60° C., and the duration is 10 minutes, in the case of a product having a pH of 4.0 to 4.6, the temperature is 85° C., and the duration is 30 minutes, and in the case of a product having a pH equal to or higher than 4.6, the temperature is 120° C., and the duration is equal to or longer than 4 minutes (typically, the temperature is 130° C., and the duration is equal to or longer than 30 minutes). In the case where the SIP (Step S2) requires a temperature equal to or higher than 100° C., a vapor can also be used in addition to the hot water.

(6) When one or both of the CIP (Step S1) and the SIP (Step S2) of the drink supply piping 34 of the content filling station 6 is performed, the SOP or COP (Step S4) is performed in parallel therewith on (i) the outer surface of various kinds of equipment in the container molding station 4 in the chamber 19, (ii) the outer surface of various kinds of equipment in the container sterilizing station 5 in the chamber 20, (iii) the outer surface of various kinds of equipment in the container sealing station 7 in the chamber 21, and (iv) the outer surface of various kinds of equipment in the chamber 56 for the cap sterilizing station 53.

In this process, the wheel 9 of the content filling station 6 is stopped, while the equipment, such as the wheels 10, 12, 13, 17 and 18, in the container molding station 4, the container sterilizing station 5, the container sealing station 7 and the cap sterilizing station 53 are being driven.

The SOP or COP (Step S4) is different from the SOP or COP (Steps S3 to S7) of the content filling station 6 and the other stations, and a hydrogen peroxide solution is blasted from the injection nozzles 57, 50, 52 and 54 to the outer surface of the container molding station 4, the container sterilizing station 5, the container sealing station 7 and the cap sterilizing station 53.

In this process, since the container molding station 4, the container sterilizing station 5, the container sealing station 7 and the cap sterilizing station 53 are being driven, the hydrogen peroxide solution as a working fluid spreads into every corner of the various kinds of equipment thereof to improve the cleaning effect and the sterilization effect.

(7) In the SOP or COP (Step S4) of the other stations such as the container molding station 4, the hydrogen peroxide solution may also be sprayed from the injection nozzle 45 to the content filling station 6 at rest to perform the SOP or COP (Step S3) of the content filling station 6 in parallel with the one or both of the CIP (Step S1) and the SIP (Step S2).

By spraying hydrogen peroxide at the same time as the CIP (Step S1), the outer surface of the filling nozzles 32, which have a complicated shape, can be efficiently sterilized. More specifically, even when the temperature of the filling nozzles 32 is 130° C., if the interior of the chamber 21 is dry, it is difficult to sterilize heat-resistant spore-forming bacteria because the sterilization is dry heat sterilization. However, as is obvious from FIG. 10, which shows a result of an experiment by the inventors, the outer surface of the filling valves can be easily sterilized, provided that the concentration of the hydrogen peroxide gas in the chamber 21 is equal to or higher than 5 mg/L, and the temperature of the filling valves is equal to or higher than 60° C.

When the SOP or COP (Step S4) is performed, the temperature of the atmosphere in the chamber 20 is raised by the aseptic hot air blasted into the chamber 21 described above. As a result, the hydrogen peroxide is activated, the sterilization effect of the SOP or COP (Step S4) is improved, and any excessive hydrogen peroxide solution is dried and removed by the aseptic hot air after spraying of the hydrogen peroxide solution.

(8) When the SIP (Step S2) of the interior of the drink supply piping 34 in the content filling station 6 is completed, and the coupling 44 is disconnected, the clutch described above is connected, so that the wheel 9 is allowed to rotate in association with the other wheels 13, 17 and the like. Alternatively, the wheel 9 is allowed to rotate by being driven by the dedicated servo motor for the wheel 9.

When the wheel 9 or the like starts rotating, the same SOP or COP (Steps S3, S5, S6, S7) is performed stepwise on the content filling station 6, the container sterilizing station 5, the container sealing station 7, the cap sterilizing station 53 and the container molding station 4. Steps S3, S5, S6 and S7 can be performed in any order.

(9) Supposing that Step S3 is first performed, a peracetic acid solution is sprayed from the injection nozzles 54 to the content filling station 6 during spraying of the aseptic water in Step S3.

When Step S3 is started, the wheel 9 of the content filling station 6 starts rotating along with the other wheels, and thus the filling nozzles 32 also start rotating.

Once Step S3 is performed on the content filling station 6, a predetermined working fluid such as a liquid chemical agent or aseptic water is sprayed from the injection nozzles 45 to the exterior of the content filling station 6 in a predetermined order. Since the working fluid is blasted to the rotating filling nozzles 32 and the like, the outer surface of the filling nozzles 32 and the like is efficiently cleaned and sterilized.

The SOP or COP of Step S3 may be a process of deactivating bacteria by using warm water or the like of a temperature equal to or higher than 60° C. and lower than 100° C. instead of the sterilizer.

In Step S3, the peracetic acid solution as a sterilizer is first blasted from the injection nozzles 45 to the content filling station 6 to sterilize the outer surface of the content filling station 6, and aseptic water is then blasted to wash any excessive peracetic acid as a sterilizer or dirt from the surface of the content filling station 6.

(10) Supposing that Steps S5 to S7 are then successively performed, injection of the peracetic acid solution in Steps S5 to S7 is performed stepwise at predetermined time intervals after the start of the injection of the peracetic acid solution in Step S3. This ensures that an appropriate amount of peracetic acid is blasted without shortage of supply thereof to each of the content filling station 6, the container sterilizing station 5, the container sealing station 7, the cap sterilizing station 53 and the container molding station 4.

(11) Once the injection of the hydrogen peroxide solution in Steps S5 to S7 is completed, aseptic water is then successively blasted in steps S3, S5, S6 and S7 to the content filling station 6, the container sterilizing station 5, the container sealing station 7 and the container molding station 4 in this order. This ensures that an appropriate amount of aseptic water is supplied without shortage of supply thereof to each of the content filling station 6, the container sterilizing station 5, the container sealing station 7, the cap sterilizing station 53 and the container molding station 4.

(11) In this way, the aseptic filling apparatus is decontaminated by performing the CIP (Step S1), the SIP (Step S2) and the SOP or COP (Steps S3, S4, S5, S6, S7) of the parts of the aseptic filling apparatus where contamination is particularly unwanted.

In addition, the aseptic air continues being blasted into the chamber 21 to keep the surroundings of the content filling station 7 at a positive pressure. The aseptic air further flows to the container molding station 4, the container sterilizing station 5 and the container sealing station 7. Thus, the aseptic condition in the chambers 19, 20 and 21 is maintained.

For the cap sterilizing station 53, the aseptic condition of the atmosphere in the chamber 56 is maintained by blasting aseptic air into the chamber 56 from another system.

As shown in FIG. 7, the time required to decontaminate the aseptic filling apparatus by the CIP (Step S1), the SIP (Step S2) and the SOP or COP (Steps S3, S4, S5, S6, S7) described in (1) to (11) above is about four hours. The time required for decontamination of conventional aseptic filling apparatuses is about six hours as shown in FIG. 11, and it can be seen that the downtime is reduced according to the present invention.

(12) After the CIP (Step S1), the SIP (Step S2) and the SOP or COP (Steps S3, S4, S5, S6, S7) described above are completed, manufacture of another kind of bottled drink is started.

The method of manufacturing another kind of bottled drink is the same as those according to the first and second embodiments described above, and detailed descriptions thereof will be omitted.

Fourth Embodiment

Figure 9:
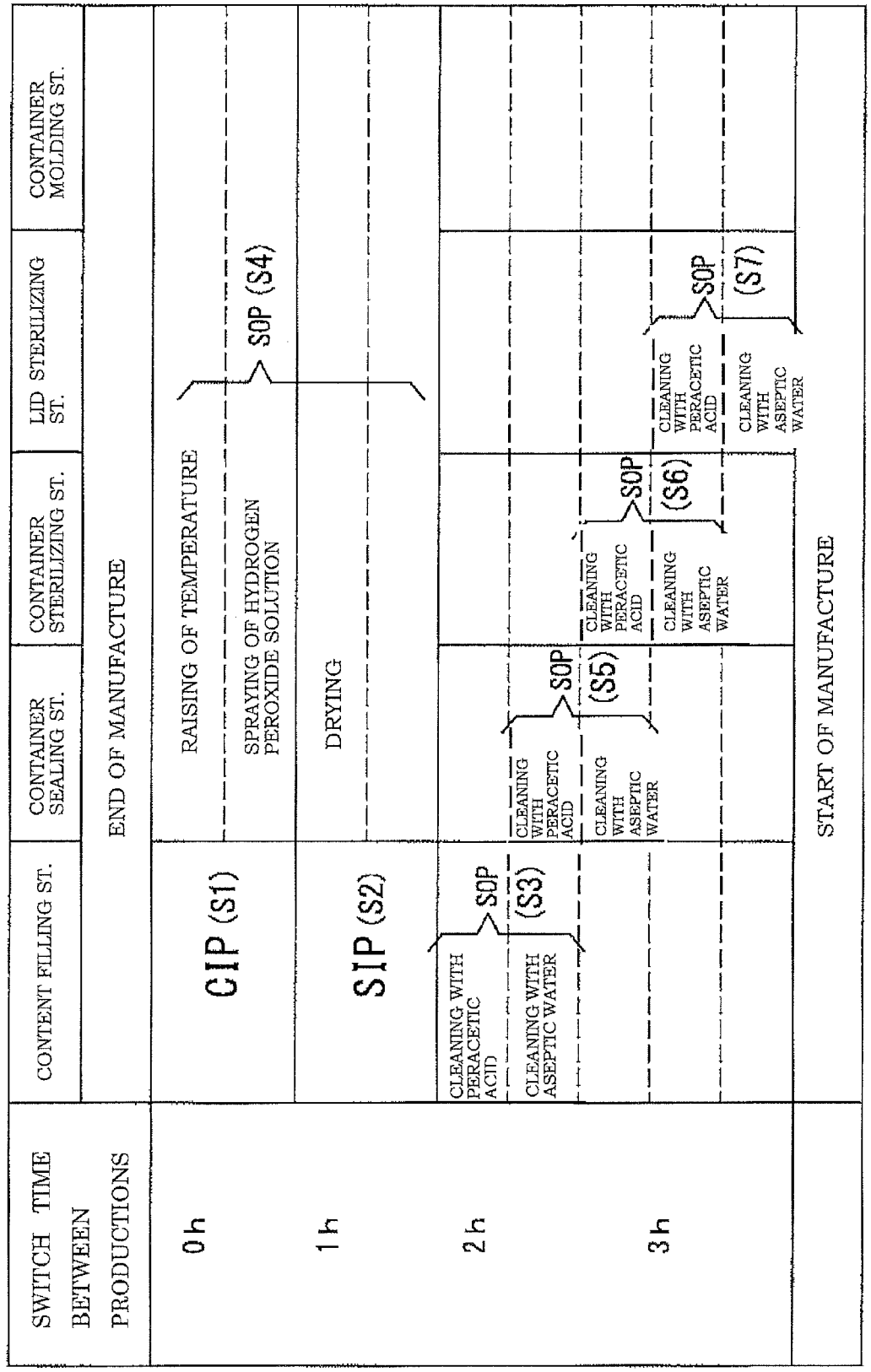
FIG. 9 is a flowchart showing another decontaminating method.

As shown in FIG. 9, according to a fourth embodiment, the CIP (Step S1), the SIP (Step S2) and the SOP or COP (Step S4) achieved by spraying a hydrogen peroxide solution are performed as in the second embodiment, the SOP or COP (Steps S3, S5, S6, S7) achieved by blasting a peracetic acid solution and aseptic water is also performed stepwise on the content filling station 6, the container sealing station 7, the container sterilizing station 5 and the cap sterilizing station 53.

However, steps S3, S5, S6 and S7 are different from those in the third embodiment in the following points.

That is, as shown in FIG. 9, a peracetic acid solution is first blasted stepwise from the injection nozzles 45, 52, 50 and 54 to the content filling station 6, the container sealing station 7, the container sterilizing station 5 and the cap sterilizing station 53 to sterilize the outer surface of the stations 7, 5 and 53, and aseptic water is then blasted stepwise to the stations 7, 5 and 53 to wash the remainder of the drink in the previous filling any excessive hydrogen peroxide solution or the like from the surface of the stations. In this process, cleaning with aseptic water in each preceding SOP or COP and cleaning with peracetic acid in the subsequent SOP or COP are performed in a temporally overlapped manner. This ensures that peracetic acid supplied in each SOP or COP is prevented from adhering to a part where peracetic acid supplied in the preceding SOP or COP is being washed and removed.

As described above, the SOP or COP (Steps S3, S5, S6, S7) of the content filling station 6, the container sterilizing station 5, the container sealing station 7 and the cap sterilizing station 53 is performed stepwise in such a manner that cleaning with aseptic water and cleaning with peracetic acid are performed in an overlapped manner, so that the downtime of the aseptic filling apparatus is further reduced, and the productivity of the bottled drink is further improved.

Fifth Embodiment

Figure 10:
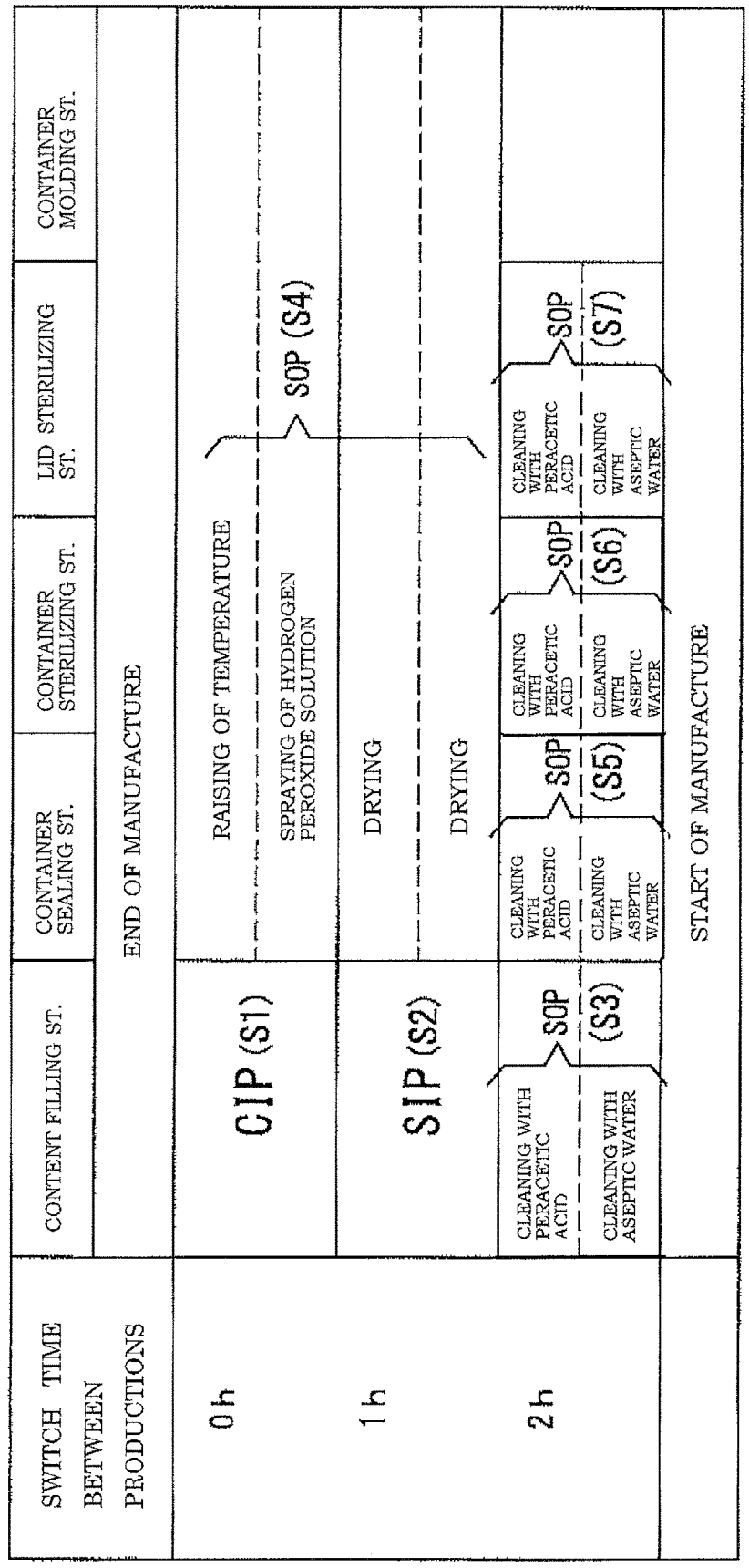
FIG. 10 is a flowchart showing further another decontaminating method.

As shown in FIG. 10, according to a fifth embodiment, although the CIP (Step S1), the SIP (Step S2) and the SOP or COP (Steps S3, S5, S6, S7) achieved by spraying a hydrogen peroxide solution are performed as in the third embodiment, the SOP or COP (Steps S3, S5, S6, S7) achieved by blasting a peracetic acid solution and aseptic water is simultaneously performed on the content filling station 6, the container sealing station 7, the container sterilizing station 5 and the cap sterilizing station 53.

Since the SOP or COP (Steps S5, S6, S7) of the container sterilizing station 5, the container sealing station 7 and the cap sterilizing station 53 is performed in parallel with the SOP or COP (Step S3) of the content filling station 6 in this way, the downtime of the aseptic filling apparatus is further reduced, and the productivity of the bottled drink is further improved.

In addition, when one or both of the CIP (Step S1) and the SIP (Step S2) of the content filling station 6 is performed, the SOP or COP (Step S4) using hydrogen peroxide of the other stations such as the container sealing station 7 is performed in parallel therewith. In this process, the wheels 17 and the like of the other stations such as the container sealing station 7 are rotating, so that the sterilization effect of the other stations such as the container sealing station 7 is improved.

Sixth Embodiment

Figure 14:
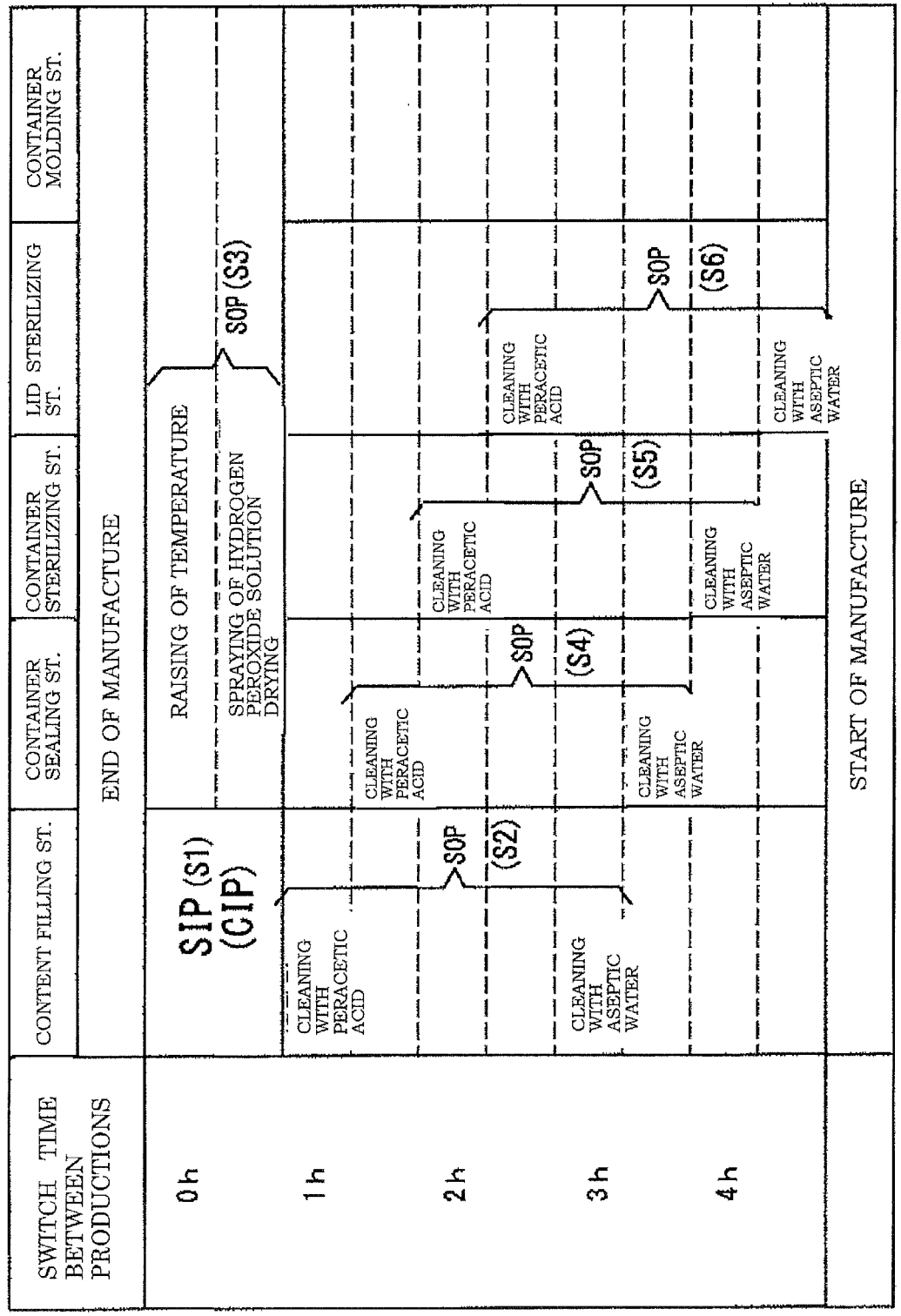
FIG. 14 is a flowchart showing a decontaminating method for the aseptic filling apparatus.

According to a sixth embodiment, as shown in FIG. 14, the controlling portion (not shown) is programmed to successively perform the SIP and the SOP or COP on the content filling station 6.

First, before starting the SIP (Step S1) of the content filling station 6, the clutch in the power transmission system of the aseptic filling apparatus is disconnected to stop rotation of only the wheel 9 in the content filling station 6, thereby stopping rotation of the filling nozzles 32.

As shown in the right half of FIG. 3, the nozzle mouth 32a of the filling nozzle 32 is then closed by the cup 42. In addition, the coupling 44 is connected. In this way, a circulation path for flowing a predetermined working fluid for the SIP such as a cleaning liquid, sterilizing liquid or water is formed.

The SIP (Step S1) is then started, and a predetermined working fluid such as an alkali cleaning liquid or water is fed from the reservoir tank 38 by the pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean and sterilize and thus decontaminate the interior of the drink supply piping 34 including the interior of the filling nozzles 32.

Figure 15:
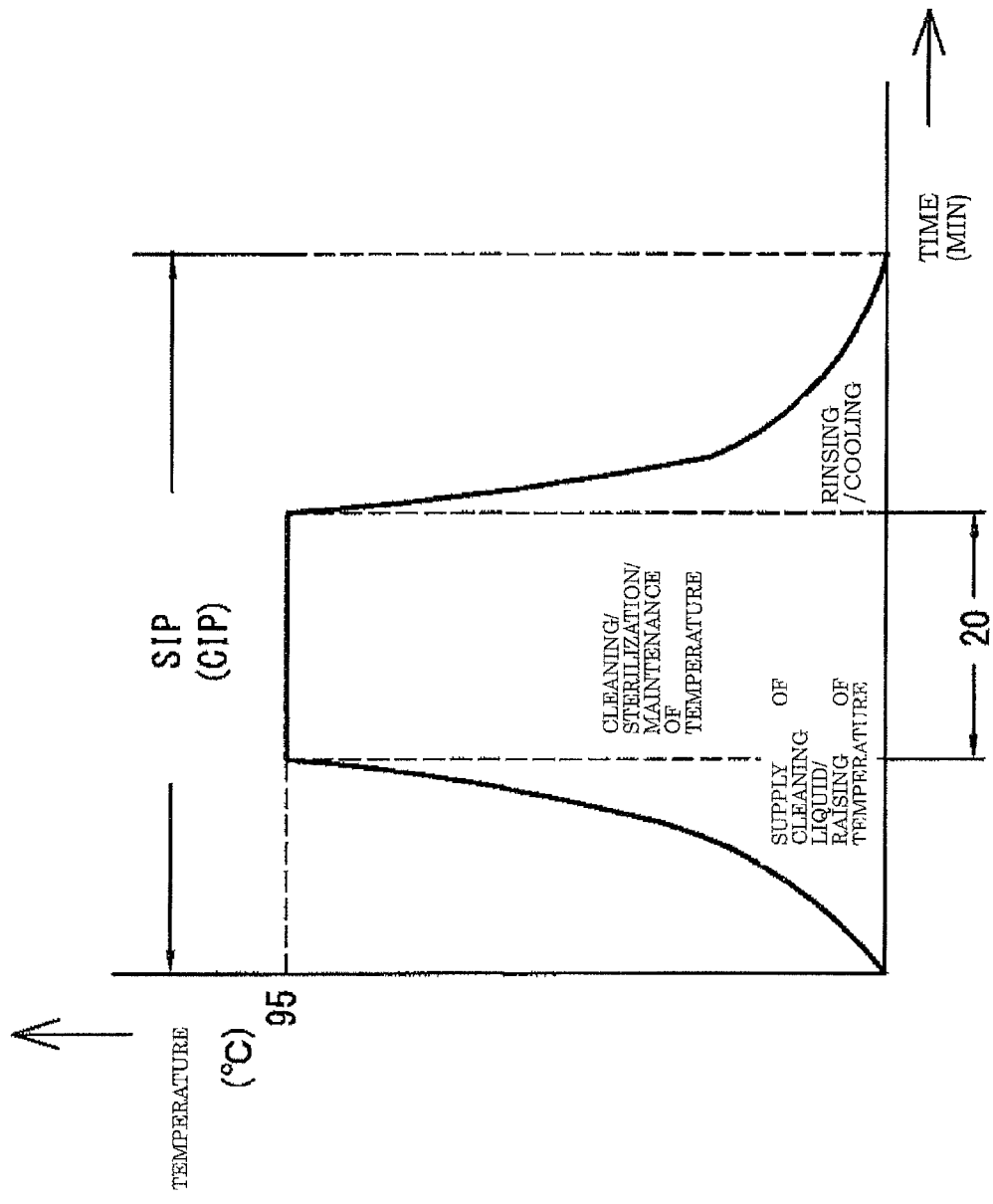
FIG. 15 is a diagram for illustrating a process of shifting from the CIP to the SIP of the interior of the drink supply piping in FIG. 14.

As shown in FIG. 15, the working fluid such as the cleaning liquid circulates in the drink supply piping 34 for 20 minutes, for example, while the working fluid is heated to about 95° C., for example. From a middle of the SIP, water is used as a cleaning liquid, which is a working fluid. The circulating working fluid cleans and sterilizes the interior of the drink supply piping 34.

After the interior of the drink supply piping 34 is sterilized, as shown in FIG. 15, the water passing through the piping is gradually cooled to room temperature.

As described above, the interior of the piping is sterilized and cleaned in the SIP (Step S1). Thus, the SIP (Step S1) serves also as the CIP, so that the conventional CIP can be omitted to substantially reduce the downtime.

Immediately after completion of the SIP (Step S1), the SOP or COP (Step S2) of the content filling station 6 is performed. The temperature required for the SIP can be a temperature and a duration that allow a sterilization value required for sterilization of the drink, which is the content of the product, to be achieved.

In FIG. 3, reference numeral 45 denotes an injection nozzle for the SOP or COP (Step S2) arranged to be opposed to each of different parts of the content filling station 6 in the chamber 21. The injection nozzles 45 are fixed to the interior of the chamber 21 at predetermined locations.

Reference numeral 46 denotes a reservoir tank, which is a supply source of a predetermined working fluid, such as a liquid chemical agent such as an alkali cleaning liquid, a peracetic acid cleaning liquid or a hydrogen peroxide solution, or aseptic water. The reservoir tank 46 is provided for each of different liquid chemical agents such as a hydrogen peroxide solution or aseptic water, although only one reservoir tank 46 is shown for convenience of drawing. Reference numerals 47 and 48 denote supply pipes extending from each reservoir tank 46 to the injection nozzle 32 described above. Each of the supply pipes 47 and 48 is provided with a pump 49.

Alternatively, the pumps 39, 49 and the like may be omitted, and the reservoir tanks 38 and 46 may be located at high elevations so that the cleaning liquid, liquid chemical agent or the like can be supplied into the chamber 21 or the like under hydrostatic pressure.

When the SIP (Step S1) of the interior of the drink supply piping 34 in the content filling station 6 is completed, and the coupling 44 is disconnected, the clutch described above is connected, so that the wheel 9 is allowed to rotate in association with the other wheels 13, 17 and the like. Alternatively, the wheel 9 is allowed to rotate by being driven by the dedicated servo motor for the wheel 9.

When the wheel 9 starts rotating, the SOP or COP (Step S2) in the chamber 21 is started.

The SOP or COP (Step S2) of the content filling station 6 in the chamber 21 is performed by blasting the sterilizer such as a peracetic acid solution from the injection nozzles 45 to the exterior of the content filling station 6 and then blasting aseptic water from the same injection nozzles 45. The sterilizer blasted to the content filling station 6 sterilizes the outer surface of the content filling station 6, and the aseptic water subsequently blasted washes the remainder of the drink in the previous filling operation and the sterilizer such as peracetic acid from the surface of the content filling station 6.

During the SOP or COP (Step S2), the filling nozzles 32 or the like rotate with the wheel 9. Since the working fluid is blasted to the rotating content filling station 6, foreign matters or the like are efficiently washed from the outer surface of the filling nozzles 32, which have a particularly complicated shape and structure, and the surface of the filling nozzles 32 is efficiently sterilized.

In the period from the start of the SIP (Step S1) to the end of the last SOP or COP (Step S6) described later, aseptic air, desirably aseptic hot air, supplied from the aseptic air supply source described above is constantly blasted to the content filling station 6 in the chamber 21. This ensures that the atmosphere in the chamber 21 is kept at a positive pressure, and the outside air containing bacteria, dust or the like is prevented from entering the chamber 21. Furthermore, the aseptic air also flows to the container sealing station 7 in the same chamber 21 and the container sterilizing station 5 in the chamber 20, so that the outside air is also prevented from entering the container sealing station 7 and the like.

The decontaminating apparatuses for the container molding station 4, the container sealing station 7, the container sterilizing station 5 and the cap sterilizing station 53 will be now described. In order to perform one or both of the SOP and COP (Steps S4, S5, S6) of the stations 4, 7, 5 and 53, as shown in FIG. 1, injections nozzles 57 having the same structure as the injection nozzles 45 are arranged at locations in the chamber 19 so as to be opposed to the container molding station 4, injection nozzles 52 having the same structures as the injection nozzles 45 are arranged at locations in the chamber 21 so as to be opposed to the container sealing station 7, injection nozzles 50 having the same structures as the injection nozzles 45 are arranged at locations in the chamber 20 so as to be opposed to the container sterilizing station 5, and injection nozzles 54 having the same structure as the injection nozzles 45 are arranged at locations in the chamber 56 so as to be opposed to the cap sterilizing station 53.

Supply pipes (not shown) extend from the reservoir tank 46 to the injection nozzles 57, 52, 50 and 54, and the supply pipes are also provided with a pump (not shown) that feeds a liquid chemical agent or the like to these pipes under pressure.

As shown in FIG. 14, the controlling portion (not shown) is programmed to perform the SOP or COP (Steps S3, S4, S5, S6) of the container molding station 4, the container sealing station 7, the container sterilizing station 5 and the cap sterilizing station 53 from the start of the SIP (Step S1) of the content filling station 6. In addition, the controlling portion is programmed to perform two types of SOP (Steps S3, S4, S5, S6) on each station.

As shown in FIG. 14, the SOP performed first (Step S3) is performed in synchronization with the SIP (Step S1) of the content filling station 6 and performed simultaneously for all of the container molding station 4, the container sealing station 7, the container sterilizing station 5 and the cap sterilizing station 53.

The SOP or COP (Step S3) is different from the SOP or COP (Step S2) of the content filling station 6 and is performed by spraying a hydrogen peroxide solution from the injection nozzles 57, 50, 52 and 54 to the outer surface of the container molding station 4, the container sterilizing station 5, the container sealing station 7 and the cap sterilizing station 53. In the SOP or COP (Step S3), the hydrogen peroxide solution may be sprayed from the injection nozzles 45 to the content filling station 6 at the same time and dried and vaporized by aseptic hot air.

In the SOP or COP (Step S3), the hydrogen peroxide solution serving as a working fluid is blasted to each of the stations 4, 5, 7 and 53 while the wheels 10, 12, 13 and the like other than the wheel 9 are rotating, so that the sterilization effect of the stations 4, 5, 7 and 53 is improved.

That is, in the SIP (Step S1), although the clutch is disconnected to stop the wheel 9 of the content filling station 6 as described above, the other wheels 17 and the like can rotate. In the alternative case, even if the dedicated servo motor for the wheel 9 of the content filling station 6 is stopped, the other wheels 17 and the like can rotate by being driven by the respective dedicated servo motors. Thus, even if the wheel 9 of the content filling station 6 is stopped when the SIP (Step S1) of the content filling station 6 is performed, the other wheels 17 and the like of the other stations such as the container sterilizing station 5 can rotate, so that the SOP or COP (Step S3, S4, S5, S6) of the outer surface of the stations other than the content filling station 6, that is, the container molding station 4, the container sterilizing station 5, the container sealing station 7 and the cap sterilizing station 53, can be effectively performed.

The sterilizer used for the SOP effectively contains 1% by mass or more of hydrogen peroxide. Alternatively, the sterilizer may contain one or more of ethanol, peracetic acid, acetic acid, octanoic acid, peroxyoctanoic acid, ozone, chlorine dioxide, chlorinated alkali and sodium hypochlorite or a mixture thereof. The sterilizer may be gas or mist, rather than liquid.

When the SOP or COP (Step S3) is performed, if aseptic hot air has been blasted into the chambers 19, 20, 21 and 56 before spraying the hydrogen peroxide solution, the temperature of the atmosphere in the chambers 19, 20, 21 and 56 increases, so that the hydrogen peroxide is activated, and the effect of sterilization by the SOP or COP (Step S3) is improved. After spraying of the hydrogen peroxide solution, the aseptic hot air promotes drying and removal of any excessive hydrogen peroxide solution.

The SOP or COP (Steps S4, S5, S6) of the container sealing station 7, the container sterilizing station 5 and the cap sterilizing station 53 that follows the SIP (Step S1) described above is the same as the SOP or COP (Step S2) of the content filling station 6 and is performed stepwise along with the SOP or COP (Step S2) of the content filling station 6.

In the SOP or COP (Steps S4, S5, S6), a peracetic acid solution is first blasted stepwise from the injection nozzles 52, 50 and 54 to the container sealing station 7, the container sterilizing station 5 and the cap sterilizing station 53 to sterilize the outer surface of the stations 7, 5 and 53.

Once the injection of the hydrogen peroxide solution is completed, aseptic water is similarly blasted stepwise to the outer surface of stations 7, 5 and 53. In this way, the remainder of the drink in the previous filling, the remainder of the peracetic acid solution and the like are washed from the surface of the stations 7, 5 and 53.

A shortage of supply of the sterilizer such as peracetic acid and the aseptic water can be prevented by injecting the hydrogen peroxide solution and the aseptic water stepwise in the SOP (or COP) as described above.

When the SOP (Step S2) of the content filling station 6 is performed, the wheel 9 of the content filling station 6 can rotate, and the other wheels 12, 13 and the like of the container sealing station 7, the container sterilizing station 5 and the cap sterilizing station 53 can also rotate. Thus, in the period from the SOP or COP (Step S2) of the content filling station 6 to the SOP (Step S6) of another station, the cleaning effect of the stations 6, 7, 5 and 53 by blasting of peracetic acid or aseptic water as a working fluid is improved.

When the SOP or COP (Steps S2, S4, S5, S6) is performed, the aseptic hot air is also blasted into the chambers 21, 20 and 56.

When the SOP or COP (Steps S2, S4, S5, S6) is performed, if the sterilizer or cleaning liquid such as peracetic acid comes into contact with the filling valves 32, heat of the filling valves 32 is lost, and thus the filling valves 32 can be poorly sterilized. To avoid this, a partition wall that prevents the sterilizer or cleaning liquid from flowing to the content filling station 6 is preferably provided between the content filling station 6 and the other stations. Alternatively, gas or mist of the sterilizer, rather than the sterilizing liquid, is preferably used for the SOP or COP in the other chambers.

Next, operations of the aseptic filling apparatus described above and a method of decontaminating the aseptic filling apparatus will be described.

(1) First, a decontamination operation of the aseptic filling apparatus will be described with reference to the flowchart of FIG. 14.

When manufacture of the bottled drink is finished, and manufacture of another kind of bottled drink is started by changing the kind of drink, the SIP (Step S1) serving also as a CIP and the SOP or COP (Steps S2, S3, S4, S5, S6) are performed on the aseptic filling apparatus.

In the period from the start of the SIP (Step S1) to the end of the last SOP (Step S6), aseptic hot air is preferably constantly blasted to the content filling station 6 in the chamber 21. This ensures that the atmosphere in the chamber 21 is kept at a positive pressure, and the outside air containing bacteria, dust or the like is prevented from entering the chamber 21. The aseptic air also flows to the container sealing station 7 in the same chamber 21 and the container sterilizing station 5 in the chamber 20, so that contamination of the container sealing station 7 and the like is also prevented. Aseptic air is also supplied into the chamber 56 for the cap sterilizing station 53.

(2) Before starting the SIP (Step S1) of the content filling station 6, the clutch in the power transmission system of the aseptic filling apparatus is disconnected to stop rotation of only the wheel 9 of the content filling station 6, thereby stopping rotation of the filling nozzles 32. In addition, the surge tank 33 is emptied.

(3) As shown in the right half of FIG. 3, the nozzle mouth 32a of the filling nozzle 32 is closed by the cup 42. In addition, the coupling 44 is connected. In this way, a circulation path for flowing a predetermined working fluid for the SIP (Step S1) such as a cleaning liquid or sterilizing liquid is formed.

(4) The SIP (Step S1) is started, and a predetermined working fluid such as an alkali cleaning liquid or water is fed from the reservoir tank 38 by the pump 39 in a predetermined order. The cleaning liquid or the like flows through the feed pipe 40 from the reservoir tank 38 to the surge tank 33, passes through the drink supply piping 34, flows into the upper manifold 37 and then to each filling nozzle 32, and eventually returns to the reservoir tank 38 through the return pipe 41. Thus, the cleaning liquid or the like flows in the circulation path for a predetermined time in a predetermined order to clean the interior of the drink supply piping 34 including the interior of the filling nozzles 32.

As shown in FIG. 15, the SIP (Step S1) is performed by first supplying an alkali cleaning liquid and flowing water in a final stage. These working fluids flow in the circulation path at a temperature of 80° C. to 95° C., for example, and is discharged from the circulation path after a lapse of 10 to 30 minutes, for example. In this way, any remaining cleaning liquid or waste liquid is removed from the drink supply piping 34, and the SIP (Step S1) is completed. The interior of the drink supply piping is sterilized and cleaned at the same time, and this means that the conventional CIP is performed at the same time. Thus, as is obvious from comparison between FIGS. 15 and 12, the idle time between the end of filling with a drink and the start of filling with another drink is reduced. However, the content to be sterilized is preferably a drink packaged in the hot packing method, such as an acidic drink having a pH lower than 4.6, mineral water, or green tea having a bacteriostatic action.

Removal of the waste liquid or the like from the interior of the drink supply piping 34 is achieved by collecting the waste liquid or the like in the reservoir tank 38 and then drawing the waste liquid from the reservoir tank 38, for example.

Conditions of the temperature of the hot water used in the SIP (Step S1) and the duration of the SIP (Step S1) are determined based on the conditions required for sterilization of the content of the product. For example, in the case of a product having a pH lower than 4, the temperature is at least 60° C., and the duration is 10 minutes, in the case of a product having a pH of 4.0 to 4.6, the temperature is 85° C., and the duration is 30 minutes, and in the case of a product having a pH equal to or higher than 4.6, the temperature is 120° C., and the duration is equal to or longer than 4 minutes (typically, the temperature is 130° C., and the duration is equal to or longer than 30 minutes). In the case where the SIP (Step S1) requires a temperature equal to or higher than 100° C., a vapor can also be used in addition to the hot water.

(5) When the SIP (Step S1) of the drink supply piping 34 of the content filling station 6 is performed, the SOP or COP (Step S3) is performed in parallel therewith on (i) the outer surface of various kinds of equipment in the container molding station 4 in the chamber 19, (ii) the outer surface of various kinds of equipment in the container sterilizing station 5 in the chamber 20, (iii) the outer surface of various kinds of equipment in the container sealing station 7 in the chamber 21, and (iv) the outer surface of various kinds of equipment in the chamber 56 for the cap sterilizing station 53.

In this process, the wheel 9 of the content filling station 6 is stopped, while the equipment, such as the wheels 10, 12, 13, 17 and 18, in the container molding station 4, the container sterilizing station 5, the container sealing station 7 and the cap sterilizing station 53 are being driven.

The SOP or COP (Step S3) is different from the SOP or COP (Steps S2, S4, S5, S6) of the content filling station 6 and the other stations, and a hydrogen peroxide solution is blasted from the injection nozzles 57, 50, 52 and 54 to the outer surface of the container molding station 4, the container sterilizing station 5, the container sealing station 7 and the cap sterilizing station 53.

In this process, since the container molding station 4, the container sterilizing station 5, the container sealing station 7 and the cap sterilizing station 53 are being driven, the hydrogen peroxide solution as a working fluid spreads into every corner of the various kinds of equipment thereof to improve the cleaning effect and the sterilization effect.

In the SOP or COP (Step S3) of the other stations such as the container molding station 4, hydrogen peroxide may also be sprayed from the injection nozzle 45 to the content filling station 6 at rest to perform the SOP or COP (Step S2) of the content filling station 6 in parallel with the SIP (Step S1).

By spraying hydrogen peroxide at the same time as the SIP (Step S1), the outer surface of the filling nozzles 32, which have a complicated shape, can be efficiently sterilized. More specifically, even when the temperature of the filling nozzles 32 is 130° C., if the interior of the chamber 21 is dry, it is difficult to sterilize heat-resistant spore-forming bacteria because the sterilization is dry heat sterilization. However, as is obvious from FIG. 10, which shows a result of an experiment by the inventors, the outer surface of the filling valves can be easily sterilized, provided that the concentration of the hydrogen peroxide gas in the chamber 21 is equal to or higher than 5 mg/L, and the temperature of the filling valves is equal to or higher than 60° C.

When the SOP or COP (Step S3) is performed, the temperature of the atmosphere in the chamber 20 is raised by the aseptic hot air blasted into the chamber 21 described above. As a result, the hydrogen peroxide is activated, the sterilization effect of the SOP or COP (Step S3) is improved, and any excessive hydrogen peroxide solution is dried and removed by the aseptic hot air after spraying of the hydrogen peroxide solution.

(7) When the SIP (Step S1) of the interior of the drink supply piping 34 in the content filling station 6 is completed, and the coupling 44 is disconnected, the clutch described above is connected, so that the wheel 9 is allowed to rotate in association with the other wheels 13, 17 and the like. Alternatively, the wheel 9 is allowed to rotate by being driven by the dedicated servo motor for the wheel 9.

When the wheel 9 or the like starts rotating, the same SOP or COP (Steps S2, S4, S5, S6) is performed stepwise on the content filling station 6, the container sterilizing station 5, the container sealing station 7, the cap sterilizing station 53 and the container molding station 4. Steps S2, S4, S5 and S6 can be performed in any order.

(8) Supposing that Step S2 is first performed, a peracetic acid solution is sprayed from the injection nozzles 54 to the content filling station 6 during spraying of the aseptic water in Step S2.

When Step S2 is started, the wheel 9 of the content filling station 6 starts rotating along with the other wheels, and thus the filling nozzles 32 also start rotating.

Once Step S2 is performed on the content filling station 6, a predetermined working fluid such as a liquid chemical agent or aseptic water is sprayed from the injection nozzles 45 to the exterior of the content filling station 6 in a predetermined order. Since the working fluid is blasted to the rotating filling nozzles 32 and the like, the outer surface of the filling nozzles 32 and the like is efficiently cleaned and sterilized.

The SOP or COP of Step S2 may be a process of deactivating bacteria by using warm water or the like of a temperature equal to or higher than 60° C. and lower than 100° C. instead of the sterilizer.

According to the sixth embodiment, in Step S2, the peracetic acid solution as a sterilizer is first blasted from the injection nozzles 45 to the content filling station 6 to sterilize the outer surface of the content filling station 6, and aseptic water is then blasted to wash any excessive peracetic acid as a sterilizer or dirt from the surface of the content filling station 6.

(9) Supposing that Steps S4 to S6 are then successively performed, injection of the peracetic acid solution in Steps S4 to S6 is performed stepwise at predetermined time intervals after the start of the injection of the peracetic acid solution in Step S2. This ensures that an appropriate amount of peracetic acid is blasted without shortage of supply thereof to each of the content filling station 6, the container sterilizing station 5, the container sealing station 7 and the cap sterilizing station 53.

(10) Once the injection of the hydrogen peroxide solution in Steps S2, S4, S5 and S6 is completed, aseptic water is then successively blasted in steps S2, S4, S5 and S6 to the content filling station 6, the container sealing station 7, the container sterilizing station 5, and the cap sterilizing station 53. This ensures that an appropriate amount of aseptic water is supplied without shortage of supply thereof to each of the content filling station 6, the container sterilizing station 5, the container sealing station 7 and the cap sterilizing station 53.

(11) In this way, the aseptic filling apparatus is decontaminated by performing the SIP (Step S1) and the SOP or COP (Steps S2, S3, S4, S5, S6) of the parts of the aseptic filling apparatus where contamination is particularly unwanted.

In addition, the aseptic air continues being blasted into the chamber 21 to keep the surroundings of the content filling station 7 at a positive pressure. The aseptic air further flows to the container molding station 4, the container sterilizing station 5 and the container sealing station 7. Thus, the aseptic condition in the chambers 19, 20 and 21 is maintained.

For the cap sterilizing station 53, the aseptic condition of the atmosphere in the chamber 56 is maintained by blasting aseptic air into the chamber 56 from another system.

As shown in FIG. 14, the time required to decontaminate the aseptic filling apparatus by the SIP (Step S1) and the SOP or COP (Steps S2, S3, S4, S5, S6) described in (1) to (10) above is about four hours. The time required for decontamination of conventional aseptic filling apparatuses is about six hours as shown in FIG. 11, and it can be seen that the downtime is reduced according to the present invention.

(12) After the SIP (Step S1) and the SOP or COP (Steps S2, S3, S4, S5, S6) described above are completed, manufacture of another kind of bottled drink is started.

The method of manufacturing another kind of bottled drink is the same as those according to the embodiments described earlier, and detailed descriptions thereof will be omitted.

Seventh Embodiment

Figure 16:
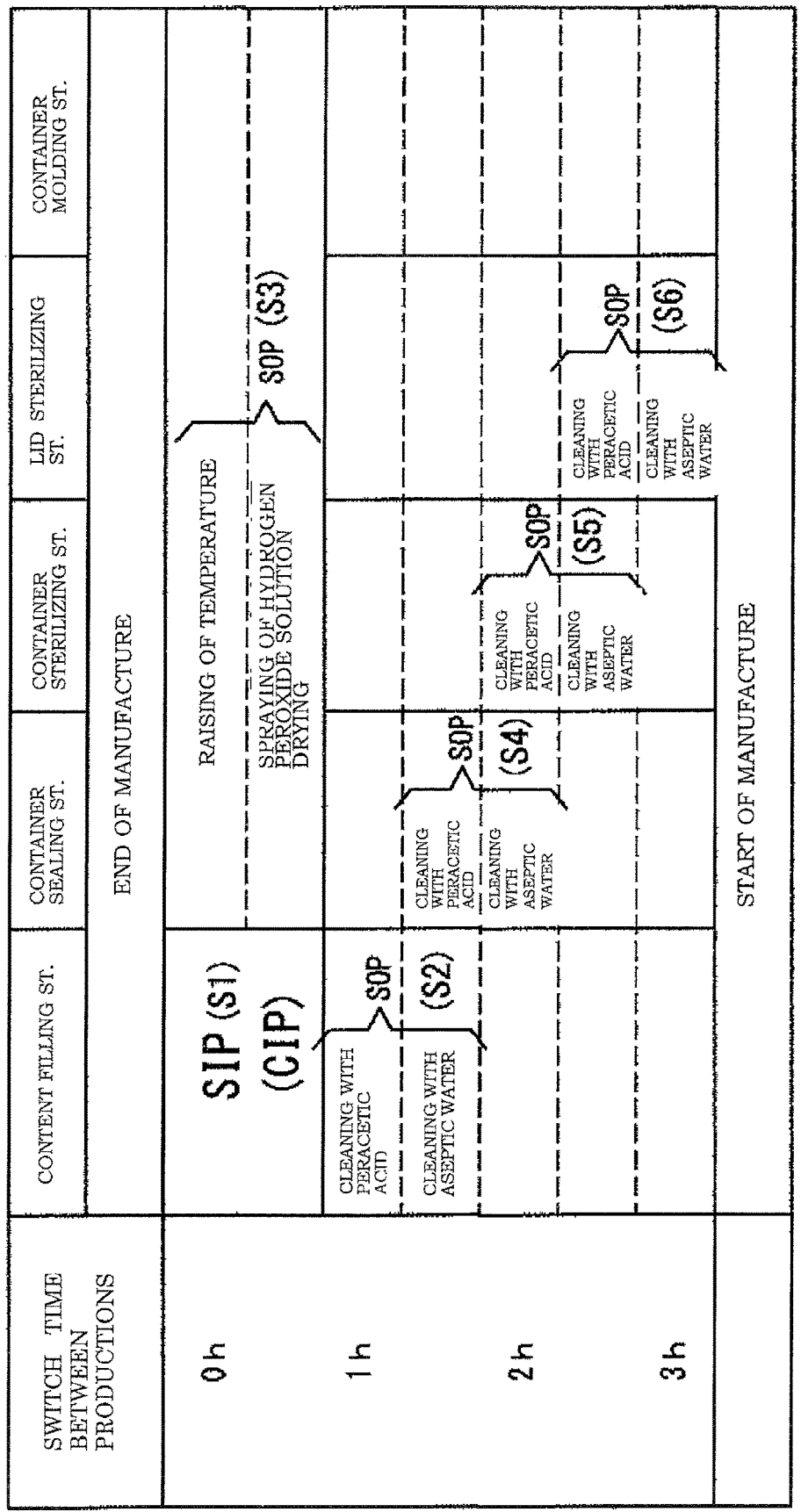
FIG. 16 is a flowchart showing another decontaminating method.

As shown in FIG. 16, according to a seventh embodiment, the SIP (Step S1) and the SOP or COP (Step S3) achieved by spraying a hydrogen peroxide solution are performed as in the sixth embodiment, the SOP or COP (Steps S2, S4, S5, S6) achieved by blasting a peracetic acid solution and aseptic water is also performed stepwise on the content filling station 6, the container sealing station 7, the container sterilizing station 5 and the cap sterilizing station 53.

However, steps S2, S4, S5 and S6 are different from those in the sixth embodiment in the following points.

That is, as shown in FIG. 16, a peracetic acid solution is first blasted stepwise from the injection nozzles 45, 52, 50 and 54 to the content filling station 6, the container sealing station 7, the container sterilizing station 5 and the cap sterilizing station 53 to sterilize the outer surface of the stations 7, 5 and 53, and aseptic water is then blasted stepwise to the stations 7, 5 and 53 to wash the remainder of the drink in the previous filling or any excessive hydrogen peroxide solution from the surface of the stations. In this process, cleaning with aseptic water in each preceding SOP or COP and cleaning with peracetic acid in the subsequent SOP or COP are performed in a temporally overlapped manner. This ensures that peracetic acid supplied in each SOP or COP is prevented from adhering to a part where peracetic acid supplied in the preceding SOP or COP is being washed and removed.

As described above, the SOP or COP (Steps S2, S4, S5, S6) of the content filling station 6, the container sterilizing station 5, the container sealing station 7 and the cap sterilizing station 53 is performed stepwise in such a manner that cleaning with aseptic water and cleaning with peracetic acid are performed in an overlapped manner, so that the downtime of the aseptic filling apparatus is further reduced, and the productivity of the bottled drink is further improved.

Eighth Embodiment

Figure 17:
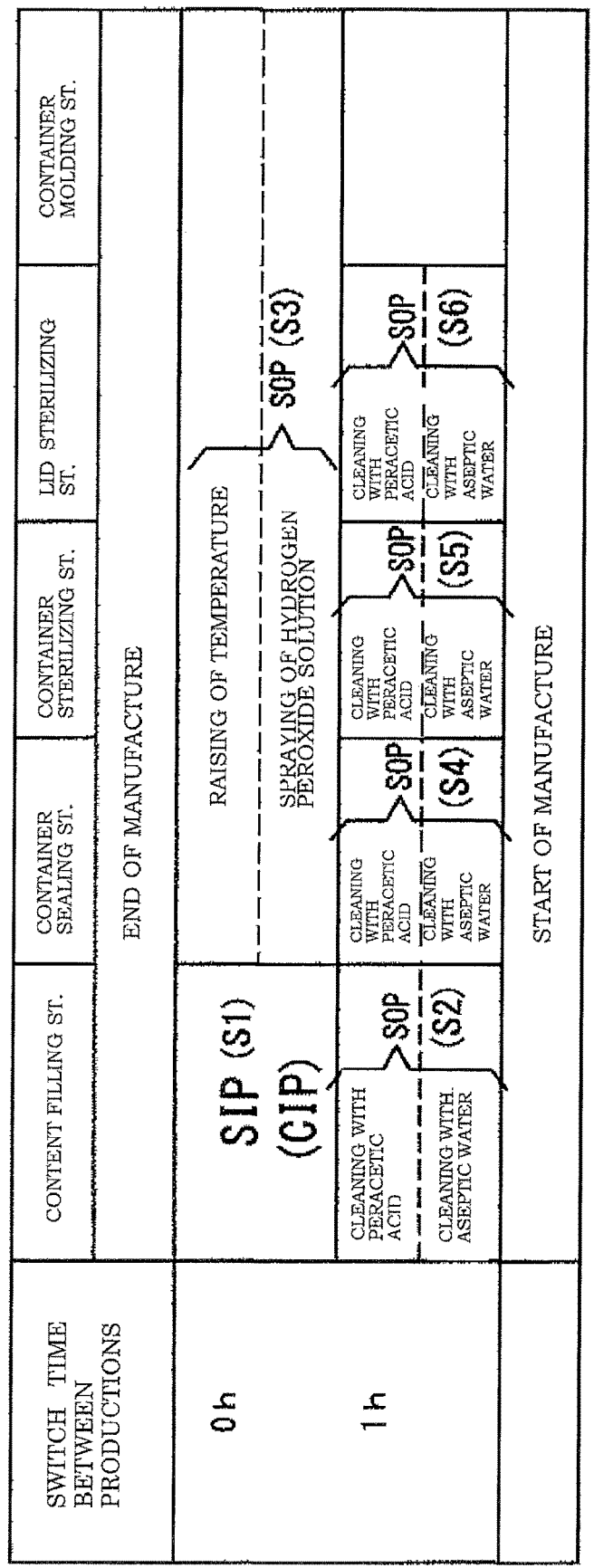
FIG. 17 is a flowchart showing further another decontaminating method.

As shown in FIG. 17, according to an eighth embodiment, although the SIP (Step S1) and the SOP or COP (Step S3) achieved by spraying a hydrogen peroxide solution are performed as in the sixth embodiment, the SOP or COP (Steps S2, S4, S5, S6) achieved by blasting a peracetic acid solution and aseptic water is simultaneously performed on the content filling station 6, the container sealing station 7, the container sterilizing station 5 and the cap sterilizing station 53.

Since the SOP or COP (Steps S4, S5, S6) of the container sterilizing station 5, the container sealing station 7 and the cap sterilizing station 53 is performed in parallel with the SOP or COP (Step S2) of the content filling station 6 in this way, the downtime of the aseptic filling apparatus is further reduced, and the productivity of the bottled drink is further improved.

In addition, when the SIP (Step S1) of the content filling station 6 is performed, the SOP or COP (Step S3) using hydrogen peroxide of the other stations such as the container sealing station 7 is performed in parallel therewith. In this process, the wheels 17 and the like of the other stations such as the container sealing station 7 are rotating, so that the sterilization effect of the other stations such as the container sealing station 7 is improved.

Although the present invention is configured as described above, the present invention is not limited to the embodiments described above, and various modifications can be made without departing from the spirit of the present invention. For example, Steps S5, S6 and 27 may be performed at the same time as Step S3. Furthermore, the container is not limited to a bottle but may be a paper container. The content is not limited to a drink but may be a liquid food, for example.

Furthermore, in FIGS. 7, 9 and 10, for example, cleaning and sterilization (S5, S6, S7) of the chambers other than that for the content filling station may be performed at the same timing as the CIP (S1) or SIP (S2) of the content filling station.

Furthermore, in FIGS. 14, 16 and 17, for example, cleaning and sterilization (S4, S5, S6) of the chambers other than that for the content filling station may be performed at the same timing as the SIP or CIP (S1) of the content filling station.

Furthermore, the container is not limited to a bottle but may be a paper container. The content is not limited to a drink but may be a liquid food, for example.

The method of sterilizing the container (bottle and cap) may be chemical agent rinse sterilization with peracetic acid or the like or electron-beam sterilization, rather than sterilization with hydrogen peroxide. The preform may be sterilized instead of sterilizing the bottle.

REFERENCE SIGNS LIST

3 container (bottle)
5 container sterilizing station
6 content filling station
7 container sealing station
9, 12, 13, 17 wheel
20, 21, 56 chamber
32 filling nozzle
51 lid (cap)
53 lid sterilizing station (cap sterilizing station)

The invention claimed is:

1. A method of decontaminating an aseptic filling apparatus, the aseptic filling apparatus comprising various kinds of stations including a content filling station arranged from an upstream side to a downstream side of a flow of a preform or container fed by rotation of wheels in a wheel train, and each of the various kinds of stations being covered by a chamber, wherein a CIP of the content filling station is performed after rotation of a wheel in the content filling station is stopped, the temperature of a cleaning liquid is raised to a temperature required for an SIP subsequent to the CIP from an early stage or a middle of the CIP, the SIP of the content filling station is performed to sterilize the content filling station and the cleaning liquid is removed with rotation of the wheel in the content filling station kept stopped, and one or both of a COP and an SOP of the content filling station is performed in a predetermined order while the wheel in the content filling station is rotating immediately after the SIP is completed.

2. The method of decontaminating an aseptic filling apparatus according to claim 1, wherein the SOP of the content filling station and the SOP of other stations are performed stepwise immediately after the SIP of the content filling station is completed.

3. The method of decontaminating an aseptic filling apparatus according to claim 2, wherein the SOP is performed by blasting of hot water or a sterilizer and blasting of aseptic water.

4. The method of decontaminating an aseptic filling apparatus according to claim 1, wherein the SOP of the content filling station and the SOP of other stations are performed in parallel with each other immediately after the SIP of the content filling station is completed.

5. The method of decontaminating an aseptic filling apparatus according to claim 1, wherein the SOP of other stations is performed while the CIP or SIP of the content filling station is being performed, and the SOP is performed by spraying of a sterilizer containing hydrogen peroxide or blasting of gas or mist of the sterilizer.

6. The method of decontaminating an aseptic filling apparatus according to claim 1, wherein aseptic air is constantly blasted to the content filling station in the chamber.

7. The method of decontaminating an aseptic filling apparatus according to claim 1, wherein a clutch that connects and disconnects transmission of power between wheels is provided between the wheel in the content filling station and a wheel in another station, and the clutch is disconnected to stop rotation of the wheel in the content filling station.

8. The method of decontaminating an aseptic filling apparatus according to claim 1, wherein the wheels in the wheel train are capable of being rotated independently of each other by a dedicated servo motor, and the dedicated servo motor is stopped to stop rotation of the wheel in the content filling station.

9. The method of decontaminating an aseptic filling apparatus according to claim 1, wherein, of the various kinds of stations, the stations other than the content filling station include at least one selected from a container molding station, a container sterilizing station, a container sealing station and a lid sterilizing station.

* * * * *